United States Patent
Dayton et al.

(10) Patent No.: US 10,245,088 B2
(45) Date of Patent: Apr. 2, 2019

(54) BONE PLATING SYSTEM AND METHOD

(71) Applicant: Treace Medical Concepts, Inc., Ponte Vedra Beach, FL (US)

(72) Inventors: Paul Dayton, Fort Dodge, IA (US); Daniel J. Hatch, Greeley, CO (US); W. Bret Smith, Lexington, SC (US); David L. Brumfield, Collierville, TN (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 363 days.

(21) Appl. No.: 14/990,368

(22) Filed: Jan. 7, 2016

(65) Prior Publication Data

US 2016/0192970 A1    Jul. 7, 2016

Related U.S. Application Data

(60) Provisional application No. 62/100,541, filed on Jan. 7, 2015, provisional application No. 62/145,964, filed on Apr. 10, 2015.

(51) Int. Cl.
*A61B 17/80* (2006.01)
*A61B 17/56* (2006.01)

(52) U.S. Cl.
CPC .......... *A61B 17/8085* (2013.01); *A61B 17/80* (2013.01); *A61B 17/8028* (2013.01); *A61B 2017/564* (2013.01)

(58) Field of Classification Search
CPC .. A61B 17/80; A61B 17/8085; A61B 17/8028
See application file for complete search history.

(56) References Cited

U.S. PATENT DOCUMENTS

| | | |
|---|---|---|
| 4,959,065 A | 9/1990 | Arnett et al. |
| 5,304,180 A | 4/1994 | Slocum |
| 5,709,686 A | 1/1998 | Talos et al. |

(Continued)

FOREIGN PATENT DOCUMENTS

| | | |
|---|---|---|
| AU | 2006252612 B2 | 4/2012 |
| CA | 2715491 C | 4/2014 |

(Continued)

OTHER PUBLICATIONS

Acumed, "Acu-Loc Wrist Plating System," Brochure and Surgical Technique, effective date Apr. 2012, reported publication date Sep. 23, 2013, 19 pages.

(Continued)

*Primary Examiner* — Christopher Beccia
(74) *Attorney, Agent, or Firm* — Fredrikson & Byron, P.A.

(57) ABSTRACT

A bone plate can be used to fixate one or more bones. In some examples, the bone plate defines an elongated body having a plurality of fixation holes arrayed at different points along the length of the body. For example, the bone plate may have opposed fixation holes separated by a bridge. The bone plate may be bent or shaped along a central longitudinal axis extending through the elongated body and also twisted around the central longitudinal axis. The bending and twisting can position each fixation hole of the elongated body in a different plane in three-dimensional space.

11 Claims, 15 Drawing Sheets

(56) References Cited

U.S. PATENT DOCUMENTS

| | | | |
|---|---|---|---|
| 5,785,712 A * | 7/1998 | Runciman | A61B 17/8085 606/283 |
| 6,540,746 B1 | 4/2003 | Buehler et al. | |
| 6,786,909 B1 | 9/2004 | Dransfeld et al. | |
| 7,175,667 B2 | 2/2007 | Saunders et al. | |
| 7,344,538 B2 | 3/2008 | Myerson et al. | |
| 7,537,596 B2 | 5/2009 | Jensen | |
| 7,695,473 B2 | 4/2010 | Ralph et al. | |
| 7,785,355 B2 * | 8/2010 | Mohr | A61B 17/8076 606/280 |
| 7,931,680 B2 | 4/2011 | Myerson et al. | |
| 8,133,283 B2 | 3/2012 | Wilson | |
| 8,162,996 B2 | 4/2012 | Schelling | |
| 8,167,918 B2 | 5/2012 | Strnad et al. | |
| 8,172,884 B2 | 5/2012 | Bouman | |
| 8,172,886 B2 | 5/2012 | Castaneda et al. | |
| 8,177,819 B2 | 5/2012 | Huebner et al. | |
| 8,177,822 B2 | 5/2012 | Medoff | |
| 8,235,994 B2 | 8/2012 | Hollawell | |
| 8,236,034 B2 | 8/2012 | Binder et al. | |
| 8,241,338 B2 | 8/2012 | Castaneda et al. | |
| 8,246,661 B2 | 8/2012 | Beutter et al. | |
| 8,257,403 B2 | 9/2012 | Den Hartog et al. | |
| 8,257,405 B2 | 9/2012 | Haidukewych et al. | |
| 8,398,687 B2 | 3/2013 | Vasta et al. | |
| 8,444,679 B2 | 5/2013 | Ralph et al. | |
| 8,512,339 B2 | 8/2013 | Medoff et al. | |
| 8,529,608 B2 | 9/2013 | Terrill et al. | |
| 8,545,540 B2 | 10/2013 | Castaneda et al. | |
| 8,702,762 B2 | 4/2014 | Jacene et al. | |
| 8,734,492 B2 | 5/2014 | Mohr et al. | |
| 8,764,807 B2 | 7/2014 | Michel et al. | |
| 8,784,498 B2 | 7/2014 | Scheland | |
| 8,808,334 B2 | 8/2014 | Strnad et al. | |
| 8,828,063 B2 | 9/2014 | Blitz et al. | |
| 8,834,532 B2 | 9/2014 | Velikov et al. | |
| 8,834,537 B2 | 9/2014 | Castaneda et al. | |
| 8,852,249 B2 | 10/2014 | Ahrens et al. | |
| 8,940,029 B2 | 1/2015 | Leung et al. | |
| 9,149,313 B2 | 10/2015 | Strnad et al. | |
| 9,220,515 B2 | 12/2015 | Castaneda et al. | |
| D765,844 S | 9/2016 | DaCosta | |
| D766,434 S | 9/2016 | DaCosta | |
| D766,437 S | 9/2016 | DaCosta | |
| D766,438 S | 9/2016 | DaCosta | |
| D766,439 S | 9/2016 | DaCosta | |
| 9,452,057 B2 | 9/2016 | Dacosta et al. | |
| 2003/0060827 A1 | 3/2003 | Coughln | |
| 2004/0116930 A1 | 6/2004 | O'Driscoll | |
| 2005/0033430 A1 | 2/2005 | Powers et al. | |
| 2005/0192578 A1 | 9/2005 | Horst | |
| 2006/0116679 A1 | 6/2006 | Lutz et al. | |
| 2006/0149264 A1 | 7/2006 | Castaneda et al. | |
| 2006/0235397 A1 | 10/2006 | Sanders et al. | |
| 2006/0241607 A1 | 10/2006 | Myerson et al. | |
| 2006/0241608 A1 | 10/2006 | Myerson et al. | |
| 2006/0276795 A1 | 12/2006 | Orbay et al. | |
| 2007/0123884 A1 | 5/2007 | Abdou | |
| 2007/0191848 A1 | 8/2007 | Wack et al. | |
| 2008/0015591 A1 | 1/2008 | Castaneda et al. | |
| 2009/0118768 A1 | 5/2009 | Sixto, Jr. et al. | |
| 2009/0210010 A1 | 8/2009 | Strnad et al. | |
| 2009/0210013 A1 | 8/2009 | Kay et al. | |
| 2009/0222047 A1 | 9/2009 | Graham | |
| 2009/0281543 A1 | 11/2009 | Orbay et al. | |
| 2010/0004691 A1 | 1/2010 | Amato et al. | |
| 2010/0023010 A1 | 1/2010 | Nelson et al. | |
| 2010/0069973 A1 * | 3/2010 | Castaneda | A61B 17/1728 606/86 B |
| 2010/0125300 A1 | 5/2010 | Blitz et al. | |
| 2011/0008745 A1 | 1/2011 | McQuillan et al. | |
| 2011/0087295 A1 | 4/2011 | Kubiak et al. | |
| 2011/0093017 A1 | 4/2011 | Prasad et al. | |
| 2011/0137351 A1 | 6/2011 | Huebner et al. | |
| 2011/0166607 A1 | 7/2011 | Castaneda et al. | |
| 2011/0264149 A1 | 10/2011 | Pappalardo et al. | |
| 2012/0065689 A1 | 3/2012 | Prasad et al. | |
| 2012/0265204 A1 | 10/2012 | Schmierer et al. | |
| 2013/0090695 A1 | 4/2013 | Bernstein et al. | |
| 2013/0172942 A1 | 7/2013 | Lewis et al. | |
| 2013/0226248 A1 | 8/2013 | Hatch et al. | |
| 2013/0238032 A1 | 9/2013 | Schilter | |
| 2013/0261670 A1 | 10/2013 | Laeng et al. | |
| 2014/0012887 A1 | 1/2014 | Tamano | |
| 2014/0052193 A1 | 2/2014 | Prandi et al. | |
| 2014/0081341 A1 | 3/2014 | Lin et al. | |
| 2014/0107650 A1 | 4/2014 | Dacosta et al. | |
| 2014/0107798 A1 | 4/2014 | Jeng et al. | |
| 2014/0172021 A1 | 6/2014 | Castaneda et al. | |
| 2014/0180343 A1 | 6/2014 | Gaudin | |
| 2014/0214093 A1 | 7/2014 | Courtney et al. | |
| 2014/0257291 A1 | 9/2014 | Houff | |
| 2014/0277176 A1 | 9/2014 | Buchanan et al. | |
| 2015/0032168 A1 | 1/2015 | Orsak et al. | |
| 2015/0039033 A1 | 2/2015 | Biedermann | |
| 2015/0045839 A1 | 2/2015 | Dacosta et al. | |
| 2015/0335366 A1 | 11/2015 | Dacosta et al. | |
| 2015/0359580 A1 | 12/2015 | Dacosta et al. | |
| 2016/0030098 A1 | 2/2016 | Dacosta et al. | |
| 2016/0192970 A1 | 7/2016 | Dayton et al. | |
| 2016/0235454 A1 | 8/2016 | Treace et al. | |
| 2016/0256204 A1 | 9/2016 | Patel et al. | |

FOREIGN PATENT DOCUMENTS

| | | |
|---|---|---|
| CN | 2701408 Y | 5/2005 |
| CN | 101836888 A | 9/2010 |
| CN | 201912210 U | 8/2011 |
| CN | 102755186 A | 10/2012 |
| CN | 103892954 A | 7/2014 |
| EP | 2389884 B1 | 7/2013 |
| EP | 2441406 B1 | 9/2013 |
| ES | 2379929 T3 | 5/2012 |
| IL | 184773 A | 8/2012 |
| IN | 200607174 P1 | 8/2007 |
| KR | 101081268 B1 | 11/2011 |
| WO | 2004024009 A1 | 3/2004 |
| WO | 2006065512 A1 | 6/2006 |
| WO | 2007006430 A1 | 1/2007 |
| WO | 2007106962 A1 | 9/2007 |
| WO | 2008029142 A2 | 3/2008 |
| WO | 2008029143 A2 | 3/2008 |
| WO | 2014152535 A1 | 9/2014 |
| WO | 2015094410 A1 | 6/2015 |
| WO | 2016003477 A1 | 1/2016 |
| ZA | 200808914 B | 2/2012 |

OTHER PUBLICATIONS

Acumed, "Hand Fracture System," Brochure, effective date Sep. 2014, reported publication date Jan. 29, 2016, 6 pages.

Acumed, "Hub Cap Fusion Plates," Retrieved from <http://www.acumed.net/products/hand-wrist/carpal/hub-cap-fusion-plates>, 2016, 8 pages.

Arthrex, "Plantar Lapidus Plate," 2015, 6 pages.

Arthrex, "Proximal Metatarsal Osteotomy using Plates," Retrieved from <http://www.arthrex.com/foot-ankle/proximal-metatarsal-osteotomy-using-plates>, 2016, 2 pages.

Couzens et al., "Stainless Steel Versus Titanium Volar Multi-Axial Locking Plates for Fixation of Distal Radius Fractures: A Randomised Clinical Trial," BMC Musculoskeletal Disorders, vol. 15, No. 74, Mar. 2014, 7 pages.

Diaconu et al., "Locking Plates for Fixation of Extra-Articular Fractures of the First Metacarpal Base: A Series of 15 Cases," Chirurgie de la Main, vol. 30, No. 1, pp. 26-30, Abstract only.

International Patent Application No. PCT/US2016/012462, International Search Report and Written Opinion dated Jun. 3, 2016, 12 pages.

Merete GMBH, "MetaFix OpenWedge," Retrieved from <http://www.merete-medical.com/de/produkte/fuss/hallux-valgus/metafixr-openwedge.html>, 2016, 4 pages (Google Translation).

(56) References Cited

OTHER PUBLICATIONS

Osteomed, "ExtremiLock Ankle Plating System," Brochure, published prior to Nov. 20, 2014, 6 pages.
Osteomed, "ExtremiLock Foot Plating System," Brochure, published prior to Nov. 20, 2014, 6 pages.
Osteomed, "Hand Plating System," Brochure, published prior to Nov. 20, 2014, 8 pages.
Plaass et al, "Anterior Double Plating for Rigid Fixation of Isolated Tibiotalar Arthrodesis," Foot and Ankle International, vol. 30, No. 7, Jul. 2009, pp. 631-639.
Plaass et al., "Placement of Plantar Plates for Lapidus Arthrodesis: Anatomical Considerations," Foot and Ankle International, vol. 37, No. 4, Apr. 2016, pp. 427-432.
Rochet et al., "Proximal Ulna Comminuted Fractures: Fixation Using a Double-Plating Technique," Revue de Chirurgie Orthopédique et Traumatologique, vol. 96, No. 7, Nov. 2010, pp. 800-807.
Smith & Nephew, Inc, "D-RAD Smart Pack," Single-Use Volar Distal Radius Plating System, Brochure, Jun. 2014, 8 pages.
Smith & Nephew, Inc, "EVOS Mini," Plating System, Brochure, May 2015, 12 pages.
Smith & Nephew, Inc, "Proximal Humerus Locking Plate," Peri-Loc Upper Extremity Locked Plating System, Surgical Technique, Sep. 2006, 36 pages.
Smith & Nephew, Inc, "Medial Column Fusion for Midfoot Deformity Correction," VLP Foot Variable Angle Locked Plating System, Surgical Technique, 2013, 20 pages.
Stryker, "Anchorage Plating System," Operative Technique, Rev. 2, Aug. 2015, 32 pages.
Stryker, "VariAx Foot Locked Plating System," Jun. 2008, 25 pages.
Synthes, "LCP Periprosthetic System," 2009, 8 pages.
Tornier, "Hand and Wrist," Retrieved from <http://www.tornier-us.com/upper/hand/>, 2016, 1 page.
Tornier, "CoverLoc Volar Plate," Retrieved from < http://www.tornier-us.com/upper/hand/writra003/>, 2016, 2 pages.
Tornier, "DFX Distal Fibula and DTX Distal Tibia Plates," Retrieved from < http://www.tornier-us.com/lower/ankle/anktra003/>, 2016, 2 pages.
Tornier, "CalcLock Extreme," Retrieved from < http://www.tornier-us.com/lower/foot/footra011/>, 2014, 2 pages.
U.S. Appl. No. 14/981,335, Bone Positioning and Preparing Guide Systems and Methods filed Dec. 28, 2015, 72 pages.
U.S. Appl. No. 62/293,189, Tarsal-Metatarsal Joint Procedure Utilizing Fulcrum filed Feb. 9, 2016, 78 pages.
Vilex, "The Vilex Plate System," Brochure, 2011, 4 pages.
Wright Medical Group N.V., "Foot & Ankle," Retrieved from < http://www.wright.com/physicians/foot-ankle>, 2016, 4 pages.
Wright Medical Group N.V., "DARCO Modular Rearfoot System (MRS) LPS Lapidus Plating System," Brochure, Aug. 2016, 1 page.
Zimmer, Inc. "Foot and Ankle Solutions," Retrieved from <http://www.zimmer.com/medical-professionals/products/foot-and-ankle.html>, 2014, 3 pages.
European Patent Application No. 16735405.9, Extended European Search Report dated Aug. 17, 2018, 9 pages.

\* cited by examiner

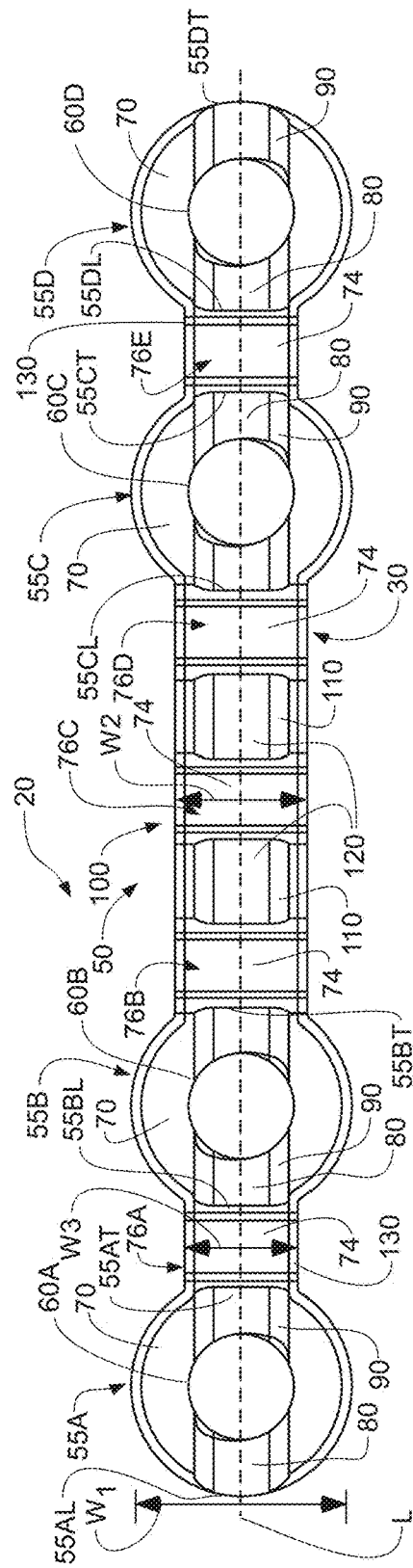

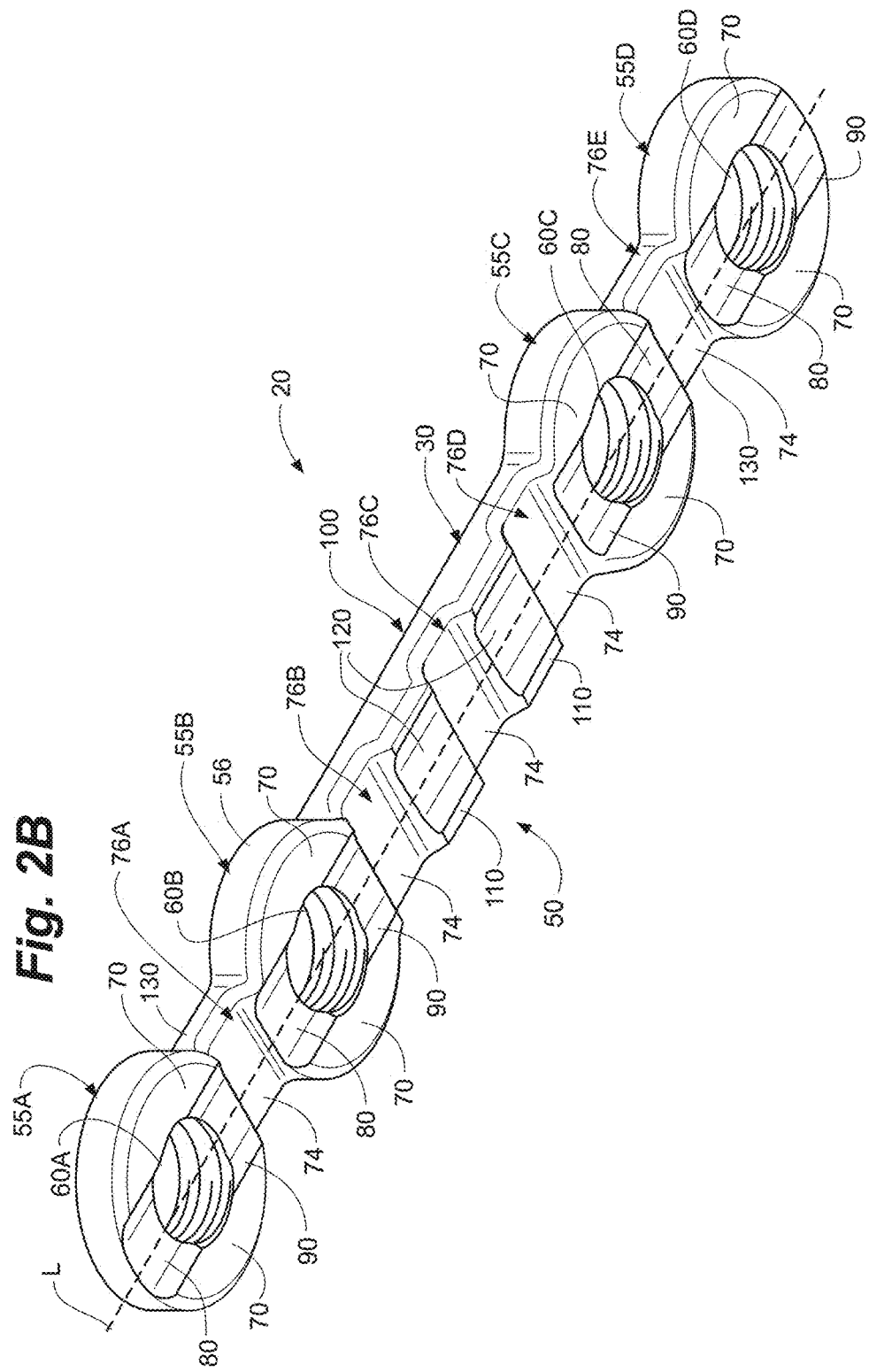

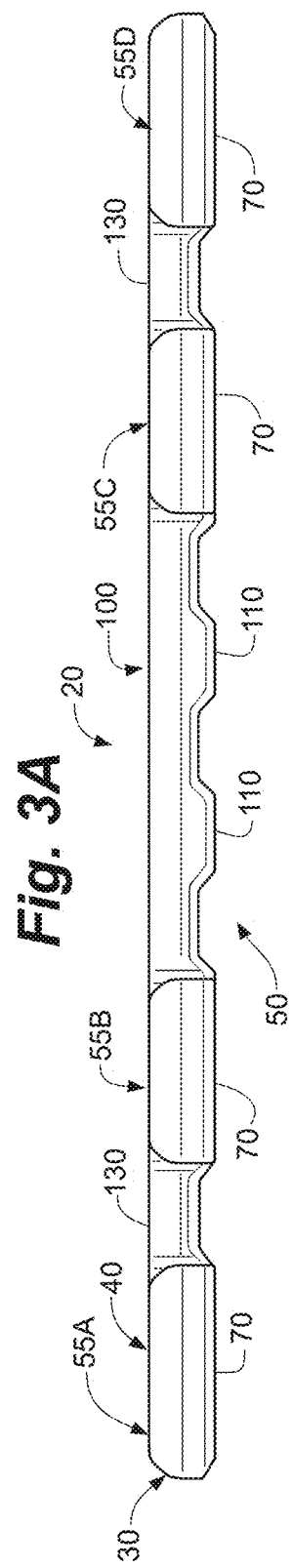
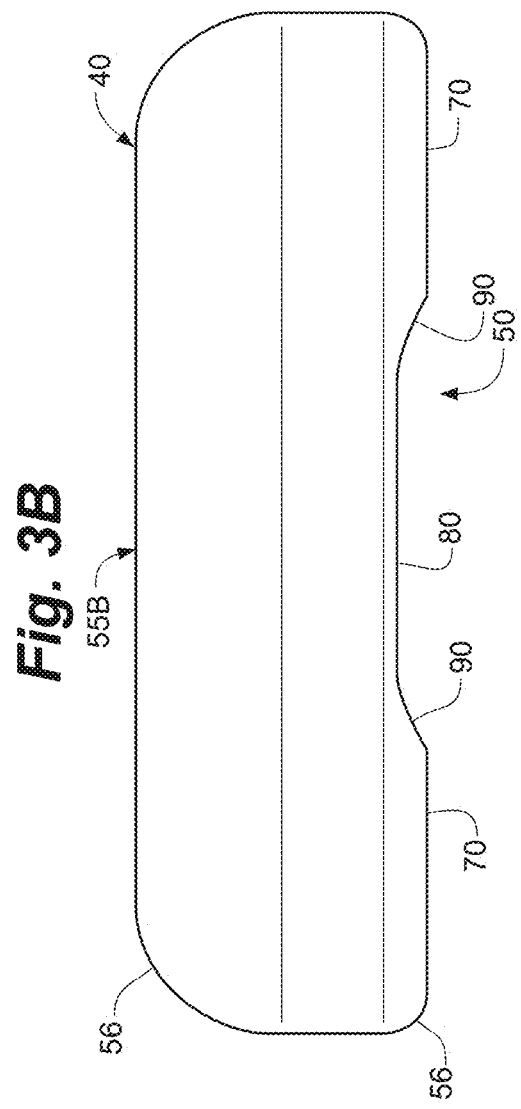

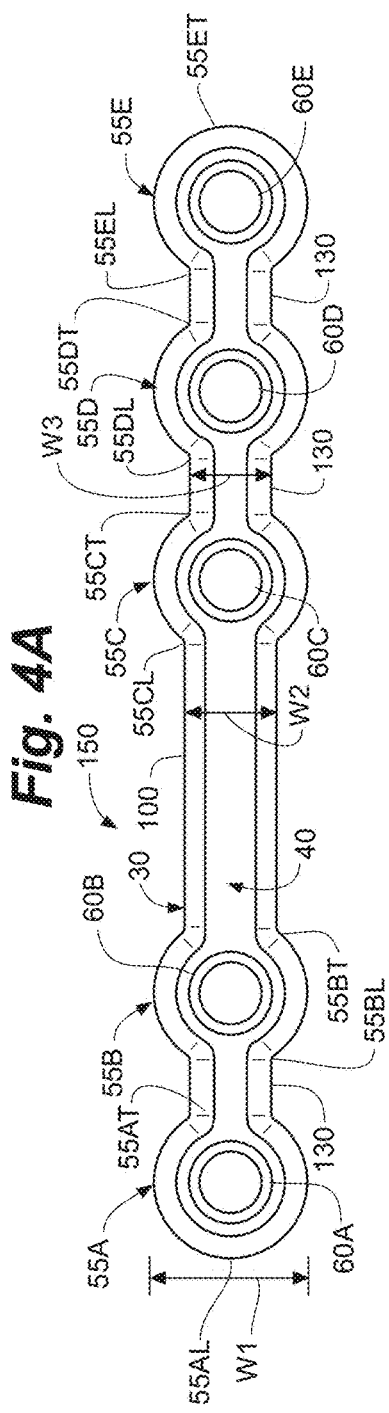
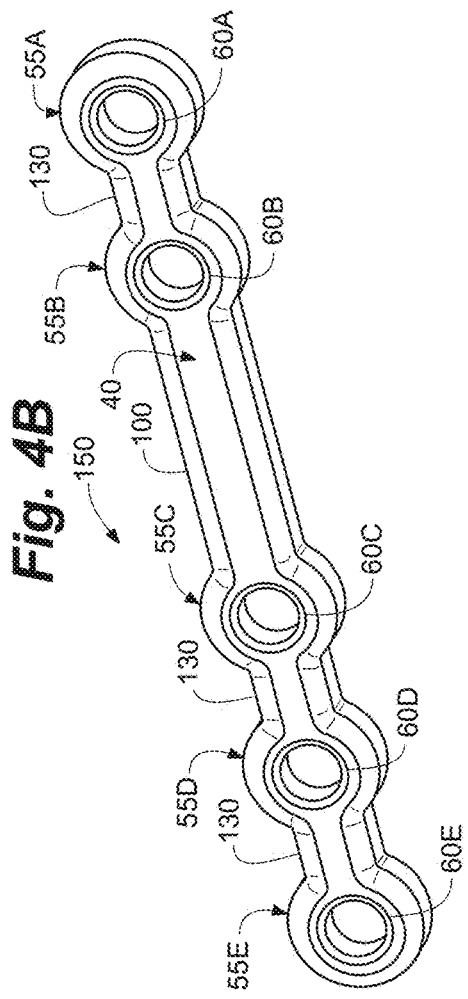

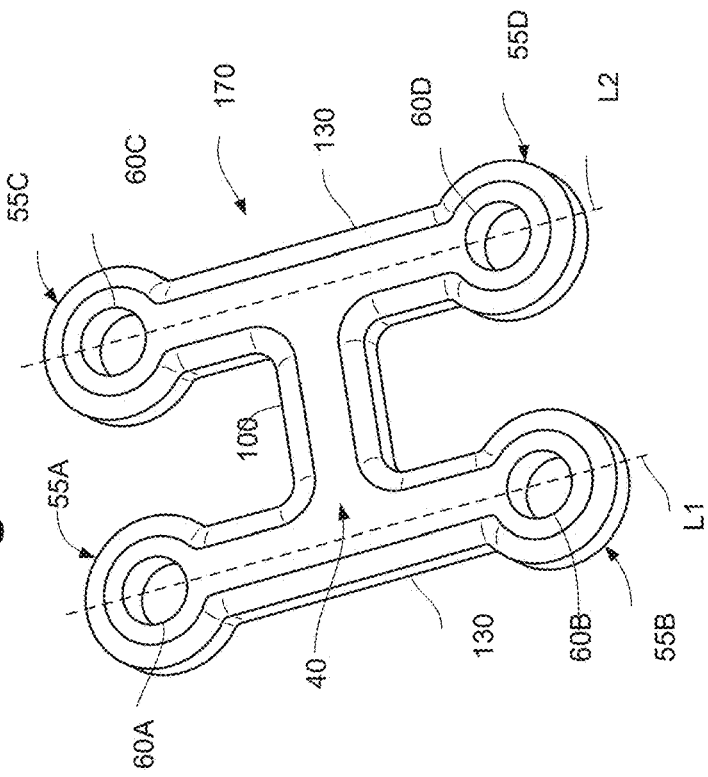
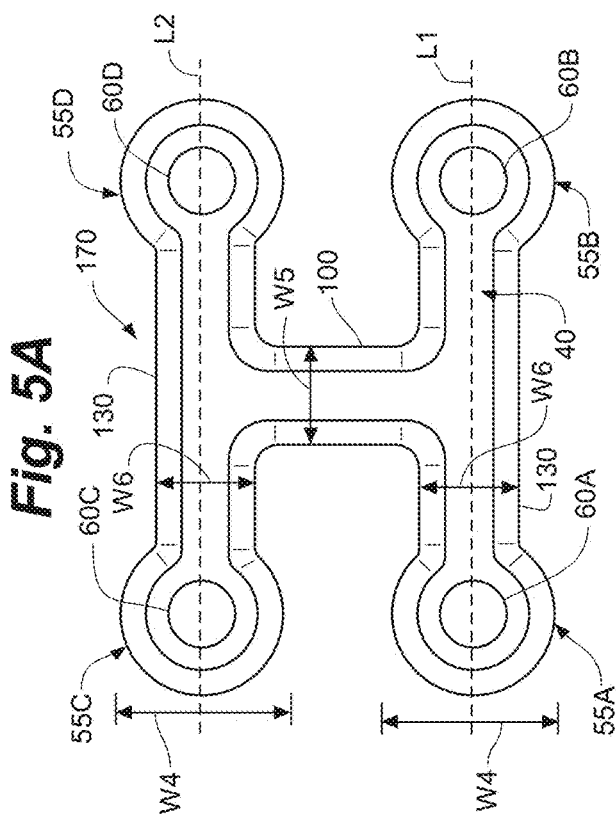

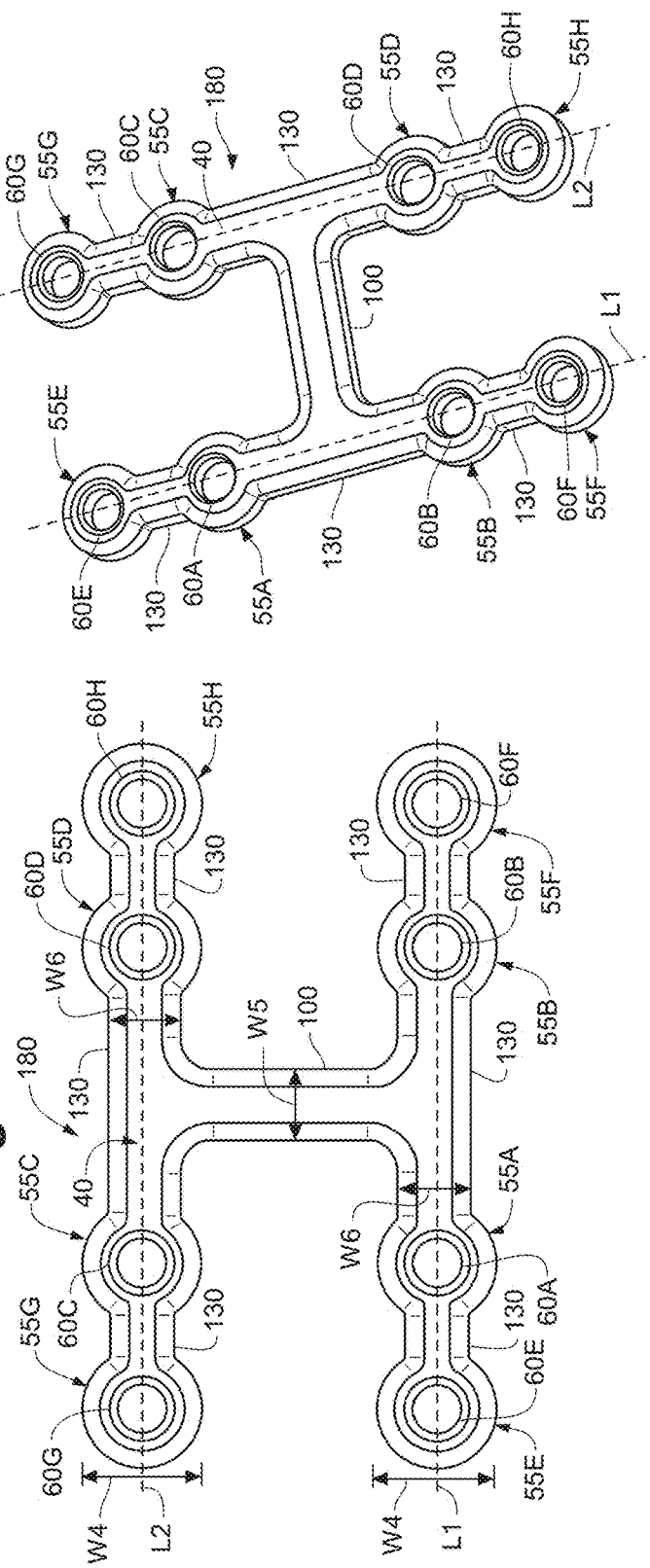

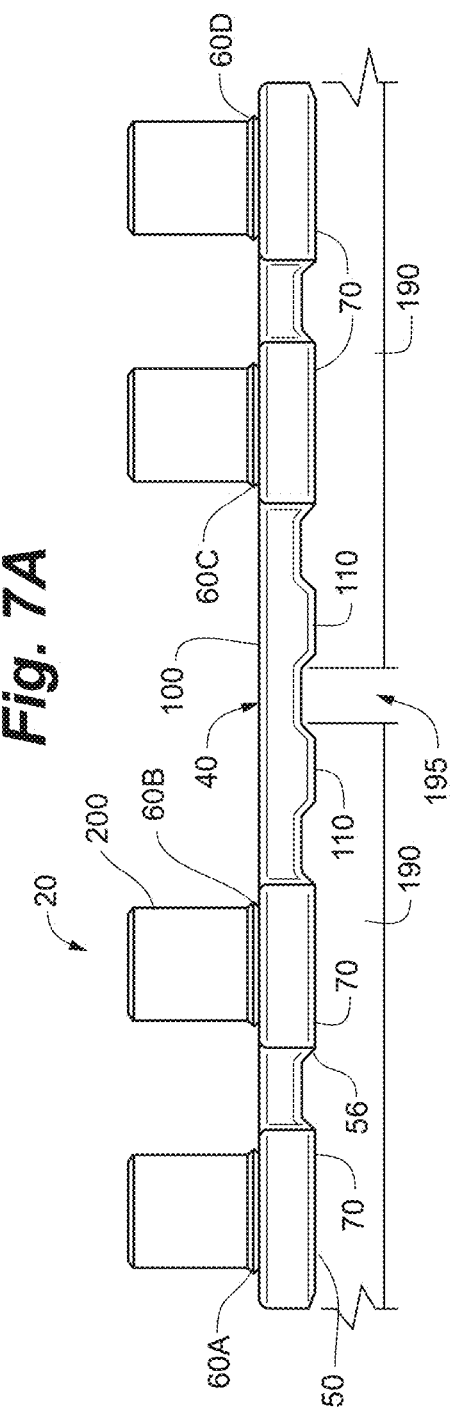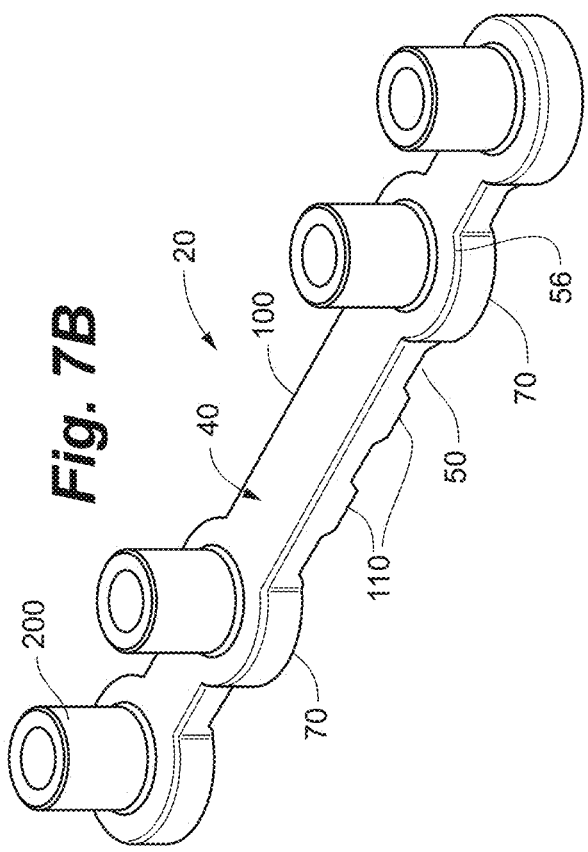

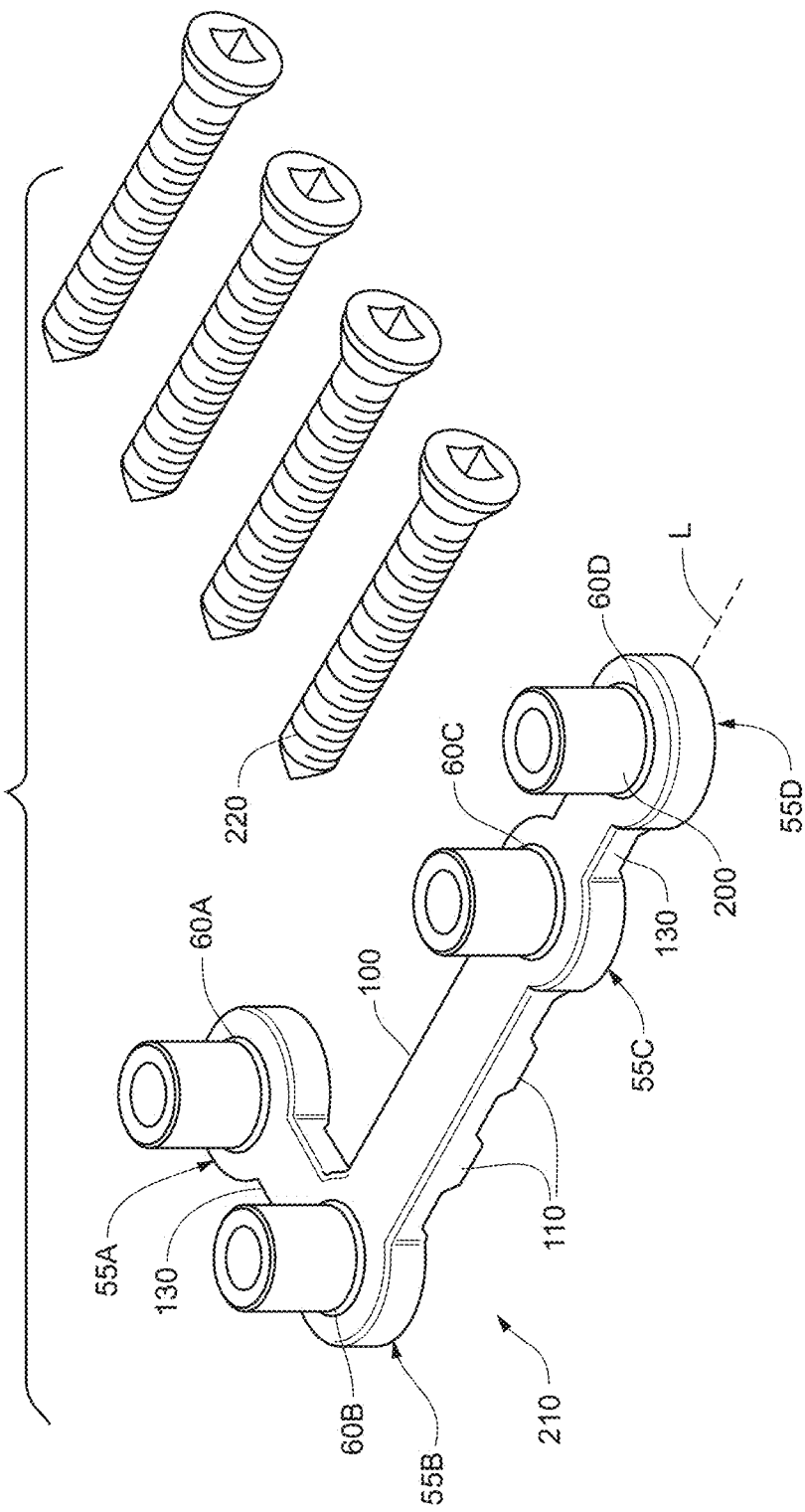

BONE PLATING SYSTEM AND METHOD

RELATED APPLICATION

This application claims the benefit of U.S. Provisional Application Ser. No. 62/100,541, filed Jan. 7, 2015 and 62/145,964, filed Apr. 10, 2015. The entire contents of both these applications are incorporated herein by reference.

TECHNICAL FIELD

This disclosure relates generally to bone plate devices and methods for fixing a bone plate device to one or more bones.

BACKGROUND

Bones, such as the bones of a foot, may be anatomically misaligned. In certain circumstances, surgical intervention is required to correctly align the bones to reduce patient discomfort and improve patient quality of life. Surgical intervention may involve cutting one or more of the misaligned bones and then physically realigning the bones into an anatomically corrected position. A bone plate or multiple bone plates may be used to hold the bones in the anatomically corrected position, helping to prevent the bones from shifting back to their misaligned position.

SUMMARY

In general, this disclosure is directed to bone plates, systems incorporating bone plates, and methods of using bone plates. In some examples, a bone plate is formed of an elongated body having a length greater than a maximum width and thickness. For example, the bone plate may have a length defining a central longitudinal axis, a width perpendicular to the central longitudinal axis, and a thickness perpendicular to both the length and width. The thickness of the bone plate may be the dimension between a top facing surface of the bone plate and a bone facing surface of the bone plate, e.g., when the bone plate is applied to one or more bones during fixation. The bone plate can have one or more fixation holes extending through the thickness of the bone plate, allowing a clinician to insert bone fasteners through the holes to secure the bone plate to the one or more bones being fixated. In addition, the bone plate can have one or more pads extending outwardly from the bone facing surface of the bone plate. The one or more pads may be positioned next to the one or more fixation holes along the length of the bone plate. For example, a pad may be positioned at least partially, and in some configurations fully, about a circumference of a region of the bone plate forming a fixation hole. As a result, the region of the bone plate defining the fixation hole may be thicker where the pad is located than adjacent locations of the bone plate not containing a pad. Configuring the bone plate with a pad in the region of the fixation hole can reduce the amount of trauma caused to the periosteal membrane of the bone or bones to which the bone plate is attached. This can help minimize blood flow disruption, helping to heal the area of the bone interfacing with the bone plate.

Although a bone plate according to the disclosure can have a variety of different configurations, in some applications, the bone plate has a helical curvature extending between opposed fixation holes. The helical curvature can cause fixation hole(s) positioned in a distal section of the bone plate to be positioned in a different plane than fixation holes(s) positioned in a proximal section of the bone plate. For example, the helical curvature may follow a path traced along an imaginary cylinder or cone at an oblique angle so as to define a spiral or curved fold. In some examples, the angle and/or extent of curvature may be formed or adjusted in-situ by fabricating the bone plate out of a malleable material. In one application, the helical curvature of the bone plate is configured to extend from the plantar region of a first metatarsal to the medial region of a medial cuneiform, thereby positioning the curvature across a metatarsal-cuneiform joint.

In one example, a bone plate is described that includes a body, one or more fixation holes, and a pad. The body has a length defining a central longitudinal axis and a width defining an extent of the bone plate transverse to the central longitudinal axis. The body includes a top surface and a bone facing surface opposite the top surface, with the bone facing surface including a first surface. The fixation hole extends through the body from the top surface to the bone facing surface. The pad extends out a distance from the first surface at a location on the bone facing surface adjacent any or all of the fixation holes.

In another example, a method of fixating a bone plate is described. The method includes positioning a bone facing surface of the bone plate in contact with a bone and contacting the bone with a pad that extends out a distance from a first surface of the bone facing surface at a location on the bone facing surface adjacent a first fixation hole. The method further includes positioning a bridge of the bone plate across a target area and inserting a first fastener through the first fixation hole and into the bone.

In another example, a bone plate is described that includes a body, a helical curvature, a first fixation hole, and a second fixation hole. The body has a length defining a central longitudinal axis extending from a proximal region of the body to a distal region of the body and a width defining an extent of the bone plate transverse to the central longitudinal axis. The body includes a top surface and a bone facing surface opposite the top surface. The helical curvature is positioned between the proximal and distal regions of the body. The helical curvature includes both a bend of the body along the central longitudinal axis and a twist of the body about the central longitudinal axis. The example specifies that the distal region lies in a first plane and the proximal region lies in a second plane offset from the first plane both along and about the longitudinal axis such that the helical curvature provides a transition from the first plane to the second plane. In addition, the example further specifies that the first fixation hole is at the proximal region, the second fixation hole is at the distal region, and the first fixation hole and second fixation hole each extend through the body from the top surface to the bone facing surface.

BRIEF DESCRIPTION OF THE DRAWINGS

FIG. 2A is a top plan view of a bone facing surface of a bone plate.

FIG. 2B is a perspective view of the bone facing surface of the bone plate of FIG. 2A.

FIG. 3A is a side elevational view of the bone plate of FIG. 2A.

FIG. 3B is a close-up, end elevational view of a portion of the bone plate of FIG. 3A.

FIG. 4A is a top plan view of a top surface of a further embodiment of a bone plate.

FIG. 4B is a perspective view of the top surface of the bone plate of FIG. 4A.

FIG. 5A is a top plan view of a top surface of another example bone plate.

FIG. 5B is a perspective view of the top surface of the bone plate of FIG. 5A.

FIG. 6A is a top plan view of a top surface of another example bone plate.

FIG. 6B is a perspective view of the top surface of the bone plate of FIG. 6A.

FIG. 7A is a side elevational view of the embodiment of the bone plate of FIG. 1 including attachment members.

FIG. 7B is a perspective view of the bone plate of FIG. 7A.

FIG. 8 is a perspective view of a further embodiment of a bone plate including attachment members and fasteners.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and dimensions are provided for selected elements, and all other elements employ that which is known to those of ordinary skill in the field of the invention. Those skilled in the art will recognize that many of the noted examples have a variety of suitable alternatives.

The present disclosure is generally directed to bone plates, systems and kits that include one or multiple bone plates, and method of using one or multiple bone plates. In an exemplary application, a bone plate according to the disclosure can be useful for internal fixation of a bone or bones during a surgical procedure, such as a bone alignment, osteotomy, fusion procedure, fracture repair, and/or other procedures where one or more bones are to be set in a desired position. Such a procedure can be performed, for example, on bones (e.g., adjacent bones separated by a joint or different portions of a single bone) in the foot or hand, where bones are relatively small compared to bones in other parts of the human anatomy. In one example, a procedure utilizing an embodiment of the bone plate can be performed to correct an alignment between a metatarsal (e.g. a first metatarsal) and a cuneiform (e.g., a first/medial cuneiform), such as a bunion correction. An example of such a procedure is a lapidus procedure. In another example, the procedure can be performed by modifying an alignment of a metatarsal (e.g. a first metatarsal). An example of such a procedure is a basilar metatarsal osteotomy procedure.

Figure 1A:
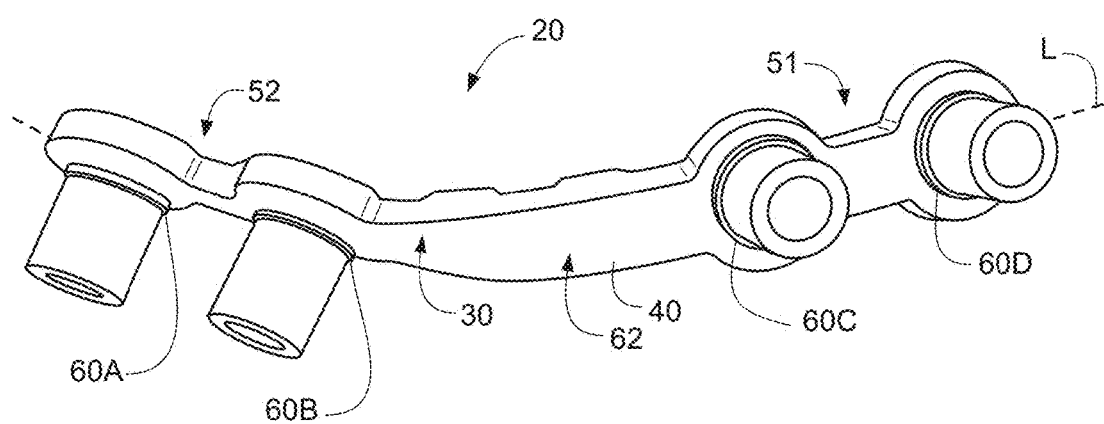
FIG. 1A is a perspective view of an example bone plate.
Figure 1B:
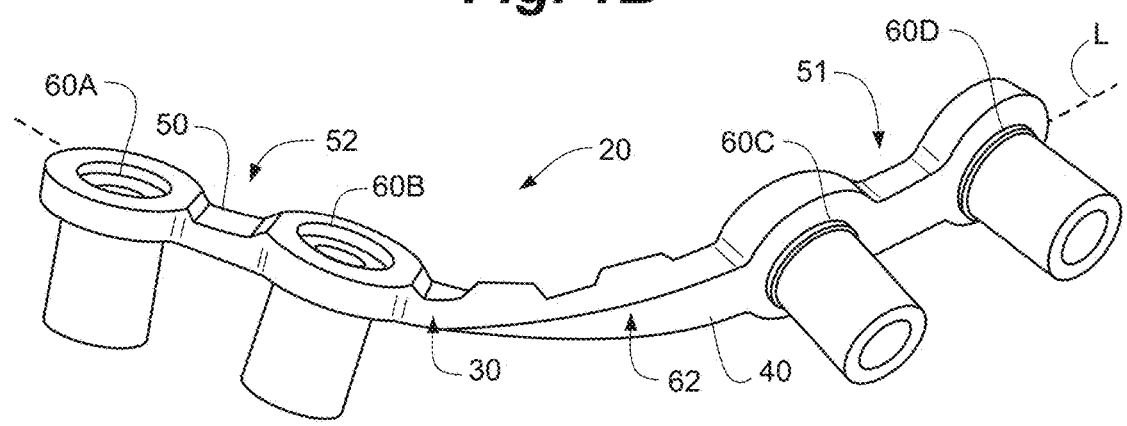
FIG. 1B is a perspective view of the bone plate of FIG. 1A, rotated to show a portion of a bone facing surface.

FIGS. 1A and 1B illustrate different perspective views of an embodiment of a bone plate 20 having a central longitudinal axis L. The bone plate 20 defines a body 30 having a top surface 40 and a bone facing surface 50, where the bone facing surface 50 is on a side of the body 30 opposite the top surface 40. In an exemplary application, the bone plate 20 can be positioned so that the bone facing surface 50 interfaces with and/or is in contact with a bone. In the example shown in FIGS. 1A and 1B, the bone facing surface 50 includes multiple surfaces projecting different distances away from top surface 40. Thus, for convenience, "bone facing surface" will refer to the side of the bone plate generally facing bone when the plate is positioned on a bone, regardless of whether there is more than one surface and regardless of whether each surface is in contact with the bone when bone plate 20 is applied.

The body 30 of the bone plate 20 has a major length which defines the central longitudinal axis L. The body 30 can include a proximal region 51 at or near a first longitudinal end and a distal region 52 at or near a second longitudinal end that is opposite the first longitudinal end of the bone plate 20. The proximal region 51 may be separated from the distal region 52 by an intermediate region. For example, the body 30 may include one or more fixation holes. In these examples, body 30 may include one or more fixation holes in proximal region 51, one or more additional fixation holes in distal region 52, and an intermediate region devoid of fixation holes positioned between proximal region 51 and distal region 52.

In the illustrated embodiment, the distal region 52 has at least one fixation hole, which is illustrated as two fixation holes 60A and 60B, and the proximal region 51 has at least one additional fixation hole, which is illustrated as two fixation holes 60C and 60D. In other examples, body 30 may include fewer fixation holes (e.g., one, none) or more fixation holes (e.g., three, four) in proximal region 51 and/or distal region 52. Moreover, the dimensions (e.g., length) of the proximal and distal regions 51, 52 can be adjusted to accommodate the particular number of fixation holes included.

In the example shown, the proximal region 51 extends longitudinally from the first longitudinal end of the bone plate 20 to an end of the fixation hole 60C on the axis L furthest from the first longitudinal end. In addition, in this example, the distal region 52 extends longitudinally from the second longitudinal end of the bone plate 20 to an end of the fixation hole 60B on the axis L furthest from the second longitudinal end. Thus, in the illustrated example, the bone plate 20 includes a region between proximal region 51 and distal region 52, specifically between the terminal edge of fixation hole 60B and the terminal edge of fixation hole 60C, which is devoid of fixation holes and is sometimes referred to herein as a "bridge."

As shown in FIGS. 1A and 1B, the body 30 of the bone plate 20 can include a helical curvature 62. Such a helical curvature can include a curve that resides in three-dimensional space. In some embodiments, the distal region 52 lies in a first plane and the proximal region 51 lies in a second plane different from, and offset from, the first plane both along and about the longitudinal axis L. Depending on the extent of the bend and/or twist of the helical curvature 62 desired for a particular application, the first plane including the distal region 52 and the second plane including the proximal region 51 can be substantially perpendicular about the longitudinal axis. In some embodiments, the radius of the helical curvature can vary as a function of longitudinal position on the body 30. In other embodiments, the radius of the helical curvature can be constant as a function of longitudinal position on the body 30. In yet other embodiments, the body 30 of bone plate 20 does not have a helical curvature but may instead be planar or bent or otherwise shaped in a non-helical shape.

In the embodiment of the bone plate 20 shown in FIGS. 1A and 1B, the helical curvature 62 includes both a bend along the central longitudinal axis L (e.g., around an axis perpendicular to axis L) and a twist about the axis L. The bend may curve the proximal region 51 of the body 30 back toward the distal region 52 of the body about an intermediate bridge section between regions 55B and 55C. For example, the bend can reduce the distance between opposite end of body 30 as compared to when body 30 is flat or planar. The radius of the bend can vary or be constant as a function of longitudinal position on the body 30, and/or be concentrated in one or more portions of the body 30, such as the portion of the body between the proximal and distal portions. In some examples, the bend ranges from approximately 10° to approximately 45°, such as from approximately 15° to approximately 35°. In other examples, the bend ranges from 45° to 135°, such as from approximately 75° to approximately 105°. Other angles of bend are also possible.

The twist of helical curvature 62 about longitudinal axis L can rotate the proximal region of body 30 relative to the distal region 52 about axis L. For example, the twist may rotate regions 55C and 55D relative to regions 55A and 55B such that regions 55C and 55D, and the corresponding fixation holes defined therein, are radially offset from regions 55A and 55B, and the corresponding fixation holes defined therein. In some embodiments, the twist is concentrated in one or more portions of the body 30, such as the portion of the body between the proximal and distal portions. Further, in some examples, the twist of the body 30 ranges from approximately 45° to less than 180° about the axis L, such as from approximately 60° to approximately 100° about the axis L, or from approximately 70° to approximately 90° about the axis L. In other examples, the twist of the body 30 ranges from 25° to 100°, such as from 35° to 65°. Other angles of twist are also possible depending on the application.

While the bone plate 20 is described as having helical curvature 62, it should be appreciated that the curvature provided by the bone plate need not be a mathematically perfect helix. Rather, the helical curvature 62 may be a generally helical shape, such as a shape that follows the general contours of a helix even if the angles of contortion do not form a perfect helix. Therefore, it should be appreciated that a bone plate described as having a helical curvature according to the disclosure may, in practice, have a generally helical shape without forming a mathematically perfect helix.

In some embodiments, the helical curvature 62 can be concentrated or entirely within a region of the body 30 between the proximal region 51 and distal region 52. Thus, any bend of the body 30 along the axis L and any twist of the body 30 about the axis L of the helical curvature 62 can begin at or near an end of the distal region 52 (e.g., begin at or adjacent fixation hole 60B) and proceed in a proximal direction toward the proximal region 51 (e.g., terminating at or adjacent fixation hole 60C). For instance, the helical curvature 62 (e.g., the bend along the axis L and the twist about the axis L) of the illustrated embodiment begins at the end of the distal region 52 and ends at the beginning of the proximal region 51. Thus, the helical curvature 62 as shown is located on a bridge portion of the body 30 between the fixation holes 60B and 60C. In such embodiments, the helical curvature 62 provides the transition of the body 30 from the first plane to the second plane. Moreover, in this embodiment, fixation holes 60A and 60B are positioned in the same plane, fixation holes 60C and 60D are also positioned in the same plane, and the plane fixation holes 60A and 60B are positioned in is offset from the plane fixation holes 60C and 60D are positioned in by helical curvature 62.

Figure 1C:
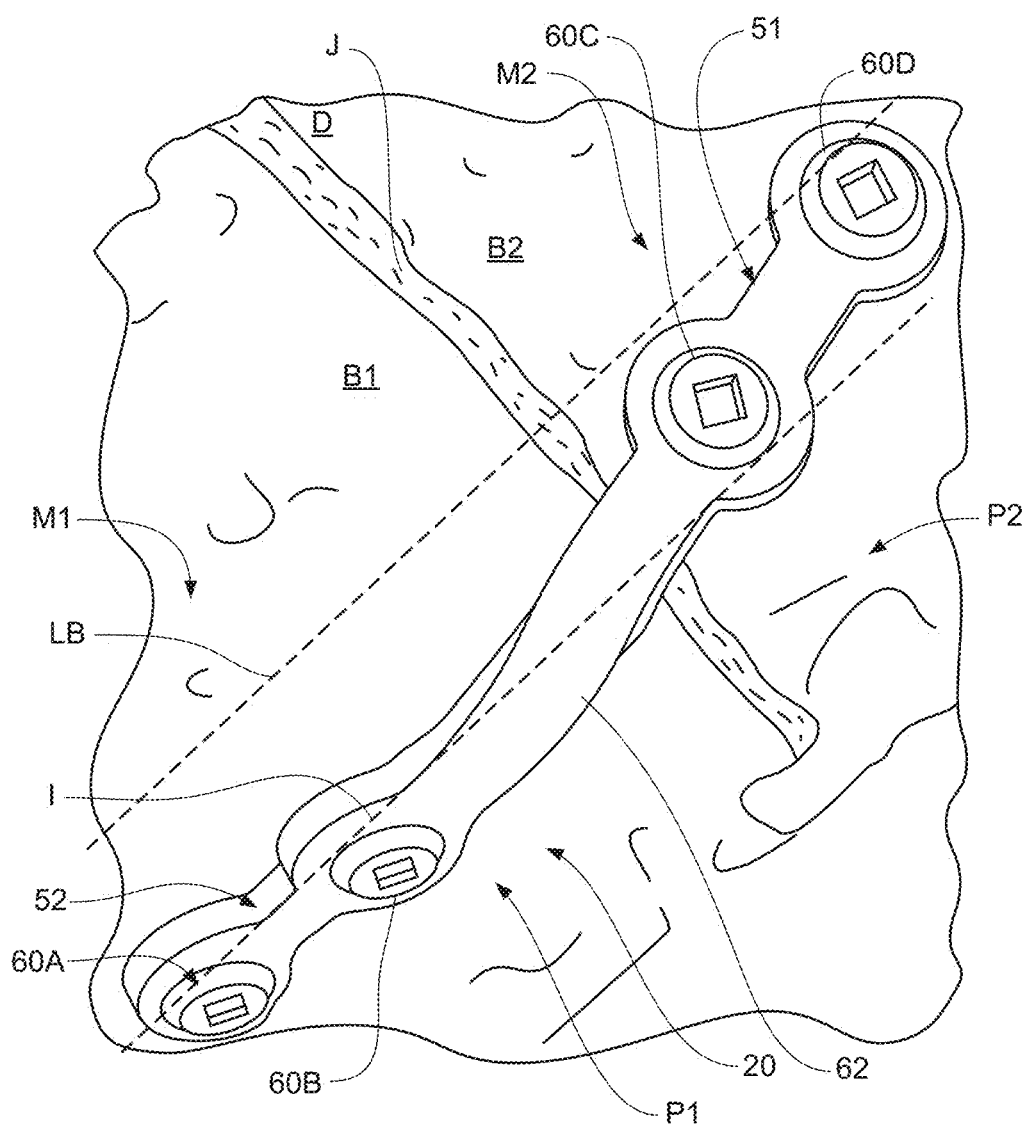
FIG. 1C is a perspective view of the bone plate of FIG. 1A shown fixed to two bones.

FIG. 1C shows a perspective view of the example bone plate 20 from FIGS. 1A and 1B fixed to two bone portions B1 and B2 across a joint J. In some applications, the bone portions B1 and B2 can be relatively small, substantially tubular members such as those bones found generally in the anatomy of the hand or foot. Bone portions B1 and B2 can be adjacent bones separated by a joint J as in the illustrated example. In other applications, the bone portions B1 and B2 can be different portions of a single bone, such as a single bone separated into portions by a fracture or other discontinuity in the single bone. Although the application of the bone plate 20 as described here may be useful for any type of one or more bones regardless of the particular anatomical location or bone geometry, this exemplary description will use the example of bones in the foot.

Using the example of bones in the foot, bone portion B1 can be, for instance, a metatarsal (e.g. a first metatarsal) while bone portion B2 can be, for instance, a cuneiform (e.g. a medial cuneiform). Bone portions B1 and B2 can each have, among other regions, respective plantar regions P1 and P2 and medial regions M1 and M2. Plantar region P1 is offset, relative to a longitudinal axis of the bones LB, from medial region M2. Similarly, plantar region P2 is offset, relative to the longitudinal axis LB, from the medial region M2. Plantar regions P1 and P2 can interface with respective medial regions M1 and M2 at interface I, which can be referred to as a dorsal-medial region. Thus, interface I may represent a location along an outer perimeter surface of each bone portion B1 and B2 where the respective plantar regions P1 and P2 transition to the respective medial regions M1 and M2.

In one example, the bone plate 20 can be positioned on a plantar region P1 or P2 of one bone portions B1 or B2 and positioned on a medial region M1 or M2 of another bone portion B1 or B2. Therefore, the bone plate 20 can cross over the interface I such that the bone plate 20 can have a portion of the body 30 on each side of the interface I. The plantar regions P1 and P2 may be any region on a plantar half of bone portion B1 and B2, respectively, while the medial regions M1 and M2 may be any region on the medial half of bone portions B1 and B2 respectively.

Figure 11:
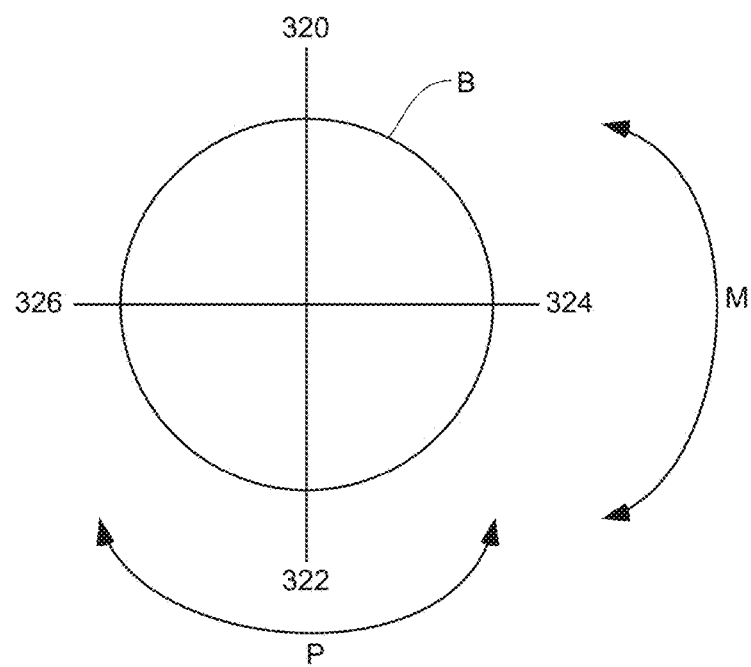
FIG. 11 is an illustration of a bone portion showing example plantar and medial regions.

FIG. 11 is an illustration of a bone portion B from the perspective of the frontal plane (e.g., looking from an anterior to a posterior direction along a metatarsal) showing an example plantar region P and medial region M that may be used as plantar regions P1 and/or P2 and medial regions M1 and/or M2 for implementing bone plate 20. As shown, the bone portion B has a dorsal position 320 and a plantar position 322, which may be the bottom, ground striking side of the bone portion. The bone portion B also has a medial position 324 and lateral position 326 (in instances where bone portion B is on the right foot; on the left foot, medial position is 326 while lateral position is 324). The medial region M may be the region of bone B on the medial side M between dorsal position 320 and plantar position 322. The plantar region P may be the region of the bone B on the plantar side between the medial position 324 and the lateral position 326.

In some examples, the bone plate 20 may be positioned on a plantar region that is more specific than the entire plantar half of the bone B. For example, the bone plate 20 may be positioned on a plantar region that ranges from the plantar position 322 to a location within a 60° arc toward the medial position 324, such as a position that ranges from the plantar position 322 to a location within a 45° arc toward the medial position 324. In some examples, the plantar region extends beyond the plantar position 322 toward the lateral position 326 in addition to extending toward medial position 324, such as a position ranging from a location within a 20° arc beyond the plantar position 322 toward the lateral position 326. For example, the plantar region may be a region formed by an arc ranging from 20° past the plantar position 322 toward the lateral position 326 and to 60° past the plantar position toward the medial position 324.

In addition to or in lieu of the plantar regions discussed above, the bone plate 20 may be positioned on a medial region that is more specific than the entire medial half of the bone B. For example, the bone plate 20 may be positioned on a medial region that ranges from the medial position 324 to a location within an arc plus or minus 45° from the medial position 324, such a location within an arc plus or minus 30° from the medial position 324.

With further reference to the embodiment shown in FIG. 1C, the bone plate 20 is configured such that the distal region 52 is positioned on the plantar region P1 of the bone portion B1 and the proximal region 51 is positioned on the medial region M2 of the bone portion B2. The body 30 of the illustrated embodiment has a portion on both sides of the interface I and transitions from the plantar region P1 to the medial region M2. In particular, the helical curvature 62 wraps about the longitudinal axis LB of the bone portion B1 (e.g., a metatarsal) starting on the plantar region P1 of the bone B1 near the distal region 52 and wraps in a medial direction toward the medial region M2 of the bone portion B2 (e.g., a cuneiform) near the proximal region 51. In other embodiments, the body can extend past the medial region to a medial-dorsal region further offset from the medial region with respect to the longitudinal axis LB. In certain embodiments, the body can extend from plantar region P1 on bone B1 to a dorsal region D on bone B2. In such embodiments, at least a portion of the body can cross a medial-lateral plane that intersects with longitudinal axis LB.

The helical curvature 62 can be included on the bone plate 20 so as to provide a twist and/or bend suitable for a particular application, e.g., such as facilitating positioning of the bone plate across the joint J and/or the interface I as described. In the example of FIG. 1C, where bone portions B1 and B2 are illustrated in the geometric configuration of a first metatarsal and medial cuneiform, respectively, the helical curvature 62 includes a twist of approximately 90° about the longitudinal axis of the bone portion B1 (and the axis L of the bone plate 20). The helical curvature 62 also includes a bend along the axis L of the bone plate 20. In combination, the curve is toward the bone portions B1 and B2 in a direction from the distal region 52 toward the proximal region 51 and away from the plantar regions P1 and P2 toward the medial regions M1 and M2.

When the helical curvature 62 of bone plate 20 is configured to wrap from a first surface (e.g., in plantar region P1) of a first bone portion (e.g., B1) to a second surface (e.g., in medial region M2) of a second bone portion (e.g., B2), the bone plate may resist separation between the first and second bone portions. For instance, where the bone portion B1 is a metatarsal and the bone portion B2 is a cuneiform, loading can act to separate the plantar regions P1 and P2, creating tensile stresses. By configured bone plate 20 to extend from the plantar region P1 at the distal region 52 to the medial region M2 at the proximal region 51, the bone plate can support the tension side across the plantar regions P1 and P2 (e.g., bottom of the foot containing bones B1 and B2 on which tension is placed). This can reduce or eliminate any gapping between the surfaces (e.g., separation between bone B1 and bone B2 and joint J) that could otherwise occur.

In some embodiments, the helical curvature 62 of the bone plate 20 is pre-formed, such that the bone plate includes the helical curvature when it is removed from its packaging. For example, helical curvature 62 may be formed in bone plate 20 before packaging, and the bone plate may be sufficiently rigid to hold the helical curvature until use. In some additional embodiments of the bone plate 20, body 30 can include malleable materials that allow for in-situ bending of the helical curvature 62. In still other embodiments, the bone plate may contain a pre-formed helical curvature 62 yet be formed of malleable materials such that the bone plate can be further bent during a surgical procedure. This can allow a clinician to adjust the radius of curvature and/or amount of bend of helical curvature 62 during a procedure to best fit the particular anatomy and/or patient undergoing the procedure (e.g., depending on the dimensions of the bones to which the bone plate 20 is to be fixed). For example, a clinician may remove the bone plate 20 from a sterile package and then bend the bone plate between proximal region 51 and distal region 52 until the shape of the helical curvature 62 best matches the anatomy across which the bone plate 20 is being positioned. In applications where bone plate 20 includes a pre-formed helical curvature 62, the amount of bending provided by the clinician may range from plus 20° (making the body 30 flatter) to minus 20°, such as from plus 10° to minus 10°, or from plus 5° to minus 5°, although other degrees of bending may also be used depending on the application.

The bone plate 20 can fabricated from any biocompatible material or combinations of materials. Example materials that the bone plate 20 may be fabricated from include metals and metal alloys, such a titanium, stainless steel, cobalt, nickel and alloys thereof (e.g., titanium-containing alloys, cobalt-containing alloys, nickel-containing alloys). The bone plate 20 may or may not be fabricated from a shape-memory alloy, such as nitinol. As another example, the bone plate 20 may be fabricated from a carbon fiber material. In general, any the foregoing materials may be configured as a material that is malleable under human hand pressure by controlling the compositional characteristics and/or thicknesses of the material.

When the bone plate 20 is fabricated from a malleable material(s) and has been positioned across the interface I as described, the body 30 can be further contoured (e.g., beyond what is provided with a pre-established helical curvature 62) to better fit a particular application. In addition, fabricating body 30 from malleable materials can allow the clinician to adjust the positioning of proximal region 51 and/or distal region 52, e.g., independent of any adjustments being made to helical curvature 62. For example, the clinician may manipulate the position of one or more of fixation holes 60A-60D relative to each other (e.g., 60A and 60B relative to each other, fixation holes 60C and 60D relative to each other, fixation holes 60A and 60D relative to each other). A clinician may desire to adjust the position of a particular fixation hole extending through body 30 to adjust the trajectory of a fixation member/bone fastener (e.g., screw) inserted through the fixation hole. In general, when the body 30 is fabricated from malleable materials, the materials may be sufficiently pliable (e.g., have a thickness and/or composition) to allow the clinician to bend the body under hand pressure but sufficiently rigid to maintain any bending applied by the clinician after removing such hand pressure.

In some examples, the proximal region 41 and/or distal region 52 can be contoured such that the fixation holes in each region (in examples where the proximal region and/or distal region contains multiple fixation holes) are in a single plane, e.g., after applying any desired contouring or bending. When so configured, bone fasteners inserted through fixation holes in a particular region (e.g., proximal region, distal region) can have parallel trajectories. In other examples, the proximal region 51 and/or distal region 52 may be contoured such that the fixation holes in each region are in different planes. When so configured, bone fasteners inserted through fixation holes in a particular region can have trajectories that are offset (e.g. "toe nail" trajectories).

To attach bone plate 20 to one or more bones, a clinician can position the bone plate on or about the one or more bones and insert bone fasteners through one or more (e.g., all) of the fixation holes 60A-D. The bone fasteners can be any mechanical fixation element that secures the bone plate to an underlying bone or bones, such as screws, pins, rivets, spikes, or the like. In one application, fixation screws are used as the bone fasteners. The fixation screws can be either locking screws or non-locking screws. Therefore, although the term "fixation screw" and "screw" is used herein, it should be appreciated that any suitable bone fastener can be used and a fixation screw is merely an exemplary bone fastener.

In the example of FIG. 1C, fixation screws are shown inserted through the fixation holes 60A and 60B at the distal region 52 in a trajectory approximately from a plantar surface P1 to an opposite dorsal surface (not shown) and through the fixation holes 60C and 60D at the proximal region 51 in a trajectory approximately from a medial surface M2 to an opposite lateral surface (not shown).

In some applications, one or more additional bone plates may be used. For example, a second bone plate (with or without a helical curvature) can be fixed to the bone portions B1 and B1. In one such example, a second bone plate is positioned from a dorsal (not shown) or medial M1 surface of the bone B1 across the joint J to a dorsal or medial M2 surface of the bone B2. In addition or alternatively, one or more cross screws may be placed through the joint J from bone B1 to bone B2 for additional bone fixation.

A bone plate as described herein can be used a part of a procedure to fixate a bone or bones. For example, a site at which the bone plate is to be applied can be prepared for application of the bone plate. A bone facing surface of the distal region of the bone plate can be positioned on a first surface of a first bone portion, and a bone facing surface of the proximal region of the bone plate can be positioned on a second surface of a second bone portion. In such applications, the first and second surfaces can be offset from each other relative to a longitudinal axis of the bone portions. In one embodiment of such a procedure, the distal region of the bone plate can be positioned on a bottom (e.g., plantar) surface of the first bone portion while the proximal region can be positioned on a side (e.g., medial) surface of the second bone portion. A helical curvature of the bone plate can span a joint or fracture between the first and second bone portions. A fastener can be inserted through a fixation hole of the proximal and/or distal region to fixate the bone plate relative to the bone portions.

FIGS. 2A-3B illustrate exemplary embodiments of the bone plate 20, which is depicted in a planar configuration to show optional features as described herein. Depending on the application, bone plate 20 can be utilized as a planar or flat bone plate, or can be bent and/or twisted to position fixation holes in different planes. FIGS. 2A and 2B illustrate a top plan view and perspective view, respectively, of the bone facing surface 50 of the body 30. FIG. 3A is a side elevational view of the bone plate 20. FIG. 3B is a close-up end elevational view of a portion of the bone plate 20.

In the illustrated example, body 30 includes the top surface 40 and the bone facing surface 50, which is on a side of the body 30 opposite the top surface 40. In an exemplary application, the bone plate 20 can be positioned so that the bone facing surface 50 contacts one or more bones. Additionally, the body 30 has a length defining the central longitudinal axis L and one or more widths W1, W2, and W3 defining an extent of the body 30 (and thus the bone plate 20). The widths W1, W2, and W3 are orthogonal to the central longitudinal axis L.

The body 30 may include regions 55A, 55B, 55C, and 55D extending from the top surface 40 to the bone facing surface 50, and which can be spaced from one another along the axis L. For instance, regions 55A and 55B can be of the distal region while regions 55C and 55D can be of the proximal region. Regions 55A, 55B, 55C, and 55D can each extend a distance along the axis L from a region leading edge 55AL, 55BL, 55CL, and 55DL to a region trailing edge 55AT, 55BT, 55CT, and 55DT, respectively. The width W1 can correspond to a width of the body 30 at each region 55A, 55B, 55C, and 55D, and in the illustrated embodiment the width W1 is the greatest extent of the body 30 transverse to the axis L.

As shown for example in FIG. 3B, region 55B has an outer shape 56 that links the top surface 40 and the bone facing surface 50. The outer shape 56 may be any type of contour at region 55B that reduces stress or increases strength of the bone plate 20. The outer shape 56 can also be used to minimize soft tissue irritation and increase bone healing during application of the bone plate 20. In the illustrated embodiment, the outer shape 56 includes a rounded edge contour that can increase strength for bending of the bone plate 20, reduce stresses in the bone plate 20 for improving the useful life of the bone plate 20, and reduce soft tissue irritation and increase bone healing when the bone plate 20 is utilized. Regions 55A, 55C, and 55D can also include outer shapes 56. Where the regions 55A, 55B, 55C, and 55D are rounded, in one embodiment one or more of the regions 55A, 55B, 55C, and/or 55D may have a radius of curvature between about 2.7 mm and about 3.0 mm (e.g., 2.9 mm). Moreover, although the regions 55A, 55B, 55C, and 55D are illustrated to be of similar sizes, the regions 55A, 55B, 55C, and 55D can also be of varying sizes. For example, one region can include the width W1 while another region may have its greatest width less than the width W1, or greater than the width W1.

Regions 55A, 55B, 55C, and 55D in FIGS. 2A-3B define fixation holes 60A, 60B, 60C, and 60D, respectively. Fixation holes 60A, 60B, 60C, and 60D extend through the body 30 at regions 55A, 55B, 55C, and 55D, respectively, from the top surface 40 to the bottom surface 50. Fixation holes 60A, 60B, 60C, and/or 60D may receive fasteners, such as bone screws. In some examples, fixation holes 60A, 60B, 60C, and/or 60D are threaded to threadingly engage fasteners or other components inserted through the holes. In other examples, fixation holes 60A, 60B, 60C, and/or 60D are not threaded but instead provide smooth bores through which fixation members are inserted. In either case, the fixation members (e.g., screws) inserted through fixation holes 60A-D may have a head and a shaft (e.g., threaded shaft), where the head has a larger cross-sectional area than the shaft. The head of the fixation members may be larger than the cross-sectional area of fixation holes 60A-D. As a result, when the fixation members are inserted through fixation holes 60A-D, the bottom surface of each head can bear against top surface 40 in regions 55A-D to fix the bone plate 20 to bone.

In the illustrated embodiment, the bone plate 20 has four regions 55A, 55B, 55C, and 55D and four fixation holes 60A, 60B, 60C, and 60D. However, any number of regions and fixation holes can be included, regardless of whether a particular region does or does not include a corresponding fixation hole extending through the region. Additionally, while the regions 55A, 55B, 55C, and 55D on the body 30 are shown as rounded, in other embodiments the regions 55A, 55B, 55C, and 55D can have other geometries.

In the illustrated example, the bone facing surface 50 includes at least one pad 70 that extends outward from first surface 74 (e.g., projects away from first surface 74 to increase the thickness of body 30 in the region of pad 70). The bone plate 20 can include pads 70 in regions 55A, 55B, 55C, and/or 55D. For example, the pads can be arrayed partially or fully about the circumference of fixation holes 60A, 60B, 60C, and/or 60D. In the embodiment shown, the first surface 74 is included on a region 76A that includes the thinnest cross-section of the bone plate 20. One or more additional regions 76B-E may be provided, each having the first surface 74 at generally the same thickness.

In one application, the pad 70 can extend outward from the first surface 74 in a direction that is generally perpendicular to the first surface 74 (e.g., in the direction of the thickness of body 30). In other applications, the pad 70 may project outward from the first surface 74 at various angles (e.g., such that the pad does not define a planar face that contacts bone but instead has an angled face). In one example, the pad extends outward about 0.3 millimeters to about 0.5 millimeters (e.g., about 0.42 millimeters) relative to the first surface 74. For instance, where the pad 70 extends out perpendicular to the surface 74 a ratio of a thickness of the bone plate 20 including the pad 70 to a thickness of the bone plate 20 at the first surface can be between approximately 1.01 and 1.5 (e.g., about 1.3).

The pad 70 can be a point of contact with a bone on the bone facing surface 50, when the bone plate 20 is applied to one or more bones. As shown, the bone facing surface 50 of the bone plate 20 includes a pad 70 at each of the regions 55A, 55B, 55C, and 55D such that the pads 70 are adjacent the fixation holes 60A, 60B, 60C, and 60D at the respective regions. In the illustrated embodiment, the pads 70 extend a length along the axis L from each region leading edge 55AL, 55BL, 55CL, and 55DL to each region trailing edge 55AT, 55BT, 55CT, and 55DT, respectively. The pads 70 as shown also extend from a first end of the width W1 of the body 30 to a first point on a perimeter of the fixation holes 60A, 60B, 60C, and 60D nearest the first end of the width W1, and from a second end of the width W1, located opposite the first end of the width W1, of the body 30 to a second point on the perimeter of the fixation holes 60A, 60B, 60C, and 60D nearest the second end of the width W1. Thus, in the embodiment shown, the pads 70 do not span an entire width, including width W1, of the regions 55A, 55B, 55C, and 55D on the bone facing surface 50. Instead, pads 70 in each of regions 55A-55D are bisected by a channel of reduced thickness (e.g., compared to pads 70) having a width equal to (or approximately equal to W3), which is the width of regions 76A-76E separating adjacent regions 55A-55D having fixation holes.

In some embodiments, the sum total of the surface area of the pads 70 is less than 50% of the total surface area of the bone facing surface area 50 of the bone plate. Although the embodiment of bone plate 20 shown includes the pads 70 adjacent the fixation holes 60A, 60B, 60C, and 60D, any number of the pads 70 can be included on the bone facing surface 50. Further, the location and geometries of the pads 70 can vary according to the particular application of the bone plate 20.

The span of the pads 70 along the width of the regions 55A, 55B, 55C, and 55D is interrupted in the embodiment of bone plate 20 by channels 80, which bisect each of the regions 55A, 55B, 55C, and 55D along the length L of body 30. In the embodiment shown, the channels 80 extend outward a distance from the first surface 74 (e.g., projects away from first surface 74 to increase the thickness of body 30 in the region of channels 80 compared to first surface 74). In other embodiments, the channels 80 can be flush with the first surface 74.

In embodiments where one or more channels 80 project out a distance from the first surface 74, the distance the channels 80 project out may be less than the distance the pads 70 project out from the first surface 74. In such embodiments, the pads 70 are raised relative to the channels 80, and the channels 80 are elevated relative to the first surface 74. That is, the thickness of the body 30 may be greater across channels 80 than across regions 76A-E defining first surface 74, and the thickness of body 30 may be greater across pads 70 than channels 80.

The channels 80 may extend a length along the axis L on the bone plate 20 from each region leading edge 55AL, 55BL, 55CL, and 55DL to each fixation hole 60A, 60B, 60C, and 60D of the respective region and from each fixation hole 60A, 60B, 60C, and 60D to each respective region trailing edge 55AT, 55BT, 55CT, and 55DT. The channels 80 may also extend a width along the width of each region 55A, 55B, 55C, and 55D between the pads 70. As such, in the illustrated embodiment, fixation holes 60A, 60B, 60C, and 60D are bounded by opposed pads 70 and opposed channels 80 along the perimeters of the fixation holes 60A, 60B, 60C, and 60D. In addition, in the illustrated example, each channel 80 in regions 55A, 55B, 55C, and 55D is aligned with the channels 80 in each other region along the axis L, providing a co-linearly aligned series of channels.

At locations where the channel 80 interfaces with the pad 70, a radiused surface 90 can be included to transition from the channel 80 to the pad 70. For example, the radiused surface 90 can provide a slope from the raised pad 70 to the relatively lower channel 80. The slope may have a constant radius of curvature or a variable radius of curvature. The radiused surface 90 may act, for example, to reduce stresses in the bone plate 20, and therefore can be useful for applications of the bone plate 20 where a greater strength is desired. In other configurations, the bone plate 20 may not have a curved transition between channel 80 and pad 70 but may instead have a sharp junction between the channel and pad.

Including one or more pads 70 and/or one or more channels 80 can provide benefits during application of the bone plate 20. For instance, including a pad 70 and/or a channel 80 on the bone facing surface 50 may decrease trauma to a periosteal membrane of a bone when the bone plate 20 is attached to a bone in a surgical procedure. Decreasing trauma to the periosteal membrane of the bone can result in less disruption of blood flow, which can help with healing the area of the bone interfacing with the bone plate 20.

Additionally, the pad 70 and/or channel 80 can increase the bending strength of the bone plate 20 without impeding the ability of a clinician to bend the bone plate 20 at a specific location (e.g., to form or modify helical curvature 62). For example, the bone plate 20 may be desirably bent at one or more of regions 76A-E to adjust position of fixation holes 60A-D relative to specific patient anatomy. In such embodiments, one or more of the regions 76A-E can be configured to concentrate bending forces applied to the bone plate. For example, regions 76A-E may be configured to concentrate bending stresses by having a smaller minimum bending force required to bend the plate at the region as compared to other regions of the plate. In the embodiment shown, the smaller minimum bending stress is provided by configuring regions 76A-E with the thinnest cross-section thickness of the plate. This can allow the bone plate 20 to be bent as desired for a particular application and anatomy without deforming any threads included in any of the fixation holes 60A-D.

In the example of FIGS. 2A-3B, bone plate 20 includes a bridge 100 extending along the axis L between regions 55B and 55C. In embodiments of the bone plate 20 that include the helical curvature, the bridge 100 can be twisted to form the helical curvature. In embodiments that do not include helical curvature 62, the bridge 100 may be planar or bent to form a curve that is not twisted. The bridge 100 may define a portion of the body 30 having a width W2. In the exemplary embodiment of the bone plate 20 shown, the width W2 along the bridge 100 can be less than the width W1 included at regions 55A, 55B, 55C, and 55D, although in other embodiments, the bridge 100 can have widths W2 equal to or greater than the width W1.

The bridge 100 as illustrated has sides running parallel to the axis L that are generally linear. In other embodiments, the bridge 100 can have rounded sides similar to the regions 55A, 55B, 55C, and 55D or any other geometry suited for the specific application of the bone plate 20. In some embodiments, the bridge is devoid of any apertures and extends between regions having fixation holes, such as regions 55B and 55C having fixation holes 60B, 60C, respectively.

The bridge 100 may include one or more pads 110 on the bone facing surface 50. The one or more pads 110 can be similar to the pad 70, such that the one or more pads 110 extend outward from the first surface 74 (e.g., increasing the thickness of body 30 in the region of the pads 110 as compared to sections of the bridge 100 that do not have pads 110). Also on the bone facing surface 50, the bridge 100 can have one or more channels 120 included along the width W2 between the pad 110. The one or more channels 120 can be similar to the channel 80.

In the embodiment shown, the channels 120 extend outward a distance from the first surface 74 (e.g., project away from first surface 74 to increase the thickness of body 30 in the region of channels 120 compared to first surface 74). In other embodiments, the channels 120 can be flush with the first surface 74. In embodiments where one or more channels 120 extend out a distance from the first surface 74, the distance the channels 120 project out may be less than the distance the pads 110 project out from the first surface 74. In such embodiments, the pads 110 are raised relative to the channels 120, and the channels 120 are elevated relative to the first surface 74, as shown in FIG. 2B. In one exemplary application, the one or more channels 120 can be aligned with the channels 80 along the axis L. Further, the one or more channels 120 can extend outward the same distance as the channels 80 from the first surface 74. In addition, the one or more channels 120 can have the same width or different width as the channels 80. Any of these embodiments can result in a continuous channel that is formed at all locations on the bone facing surface 50 along the axis L having a pad 70 or 110.

The bridge 100 shown in FIGS. 2A-3B has two pads 110: a first pad bordered by regions 76B and 76C and the second pad bordered by regions 76C and 76D. Each pad 110 has a channel 120 extending along the length L and partially across the width W2 of the pad. In other embodiments of the bone plate 20, the bridge 100 can include any number and configuration of pads 110 and channels 120. The pads 110 and channels 120 may serve similar functions to those described with respect to the pads 70 and channels 80.

Extending along the axis L between regions 55A and 55B as well as between regions 55C and 55D are branches 130. The branches 130 form a portion of the body 30 that connects the region 55A to the region 55B as well as the region 55C to the region 55D. The branches 130 have a width W3. The width W3 of the branches 130 as illustrated in less than the width W1 and W2, but in other embodiments the width W3 can be equal to or greater than the width W1 and/or the width W2. Thus, for the bone plate 20 illustrated in FIGS. 2A-3B, the width of the body 30 is greatest at the regions 55A, 55B, 55C, and 55D and least at branches 130. The branches 130 as shown have sides running parallel to the axis L that are generally linear. In other embodiments, the branches 130 can have rounded sides similar to the regions 55A, 55B, 55C, and 55D or any other geometry suited for the specific application of the bone plate 20. In the embodiment shown, the branches define first surface 74 and coincide with regions 76A and 76E.

FIGS. 4A and 4B illustrate a further embodiment of a bone plate 150, where like reference numerals refer to like components discussed above with respect to FIGS. 1-3B. FIGS. 4A and 4B show a top plan view and a perspective view, respectively, of the top surface 40 of the bone plate 150. The bone plate 150 is similar to the previously described bone plate 20. However, the bone plate 150 includes an additional region 55E having an additional fixation hole 60E. The region 55E extends from a leading edge 55EL to a trailing edge 55ET along the length of body 30. In addition, the region 55E is connected to the region 55D by an additional branch 130. Consequently, the bone plate 150 can have a greater length than the bone plate 20 and can be beneficial, for instance, in applications where a bone plate is needed to fixate to a larger area. Bone plate 150 can have the same or similar features as that described for the bone plate 20, and can have regions configured for bending the same as or similar to those described for the bone plate 20.

FIGS. 5A and 5B show another embodiment of a bone plate 170, where like reference numerals refer to like components discussed above with respect to FIGS. 1-3B. FIGS. 5A and 5B illustrate a top plan view and a perspective view, respectively, of the top surface 40 of the bone plate 170. The bone facing surface of the bone plate 170 can have the same or similar features as those described with respect to the bone facing surface 50 of the bone plate 20, and can have regions configured for bending the same or similar to those described for the bone plate 20. The bone plate 170 has a length defining two central longitudinal axes L1 and L2. In the illustrated embodiment, the length of the bone plate 170 along both axes L1 and L2 is the same, but in other embodiments the bone plate 170 can have different lengths along the axes L1 and L2. As shown, the axes L1 and L2 are parallel, but depending on the application of the bone plate 170, the axes L1 and L2 need not be parallel.

Similar to the bone plate 20, the bone plate 170 has regions 55A, 55B, 55C, and 55D including fixation holes 60A, 60B, 60C, and 60D respectively. The pads 70 and channels 80 can be included on the bone facing surface of bone plate 170 (not illustrated) at the regions 55A, 55B, 55C, and 55D as described previously.

When configured as illustrated in FIGS. 5A and 5B, one branch 130 extends along the axis L1 connecting regions 55A and 55B and another branch 130 extends along the axis L2 connecting regions 55C and 55D. The bridge 100 of the bone plate 170 connects the two branches 130. As shown, the bridge 100 extends generally perpendicular to the branches 130. In other embodiments of the bone plate 170, the bridge 100 can be skewed between the branches 130. The pads 110 and channels 120 can be included on the bone facing surface of the bridge 100 as described previously.

The bone plate 170 defines a width W4 at the regions 55A, 55B, 55C, and 55D, a width W5 along the bridge 100, and a width W6 along the branches 130. The widths W4, W5, and W6 can be dimensioned consistent with widths W1, W2, and W3, respectively, as discussed above. Other widths and thicknesses can be used depending on the desired application.

FIGS. 6A and 6B show an additional embodiment of a bone plate 180, where like reference numerals refer to like components discussed above with respect to FIGS. 1-3B. FIG. 6A illustrates a top plan view of the top surface 40 of the bone plate 180 and FIG. 6B illustrates a perspective view of the top surface 40. The bone plate 180 can be the same or similar to the bone plate 170 described previously, with the bone plate 180 providing a larger configuration. The bone facing surface of the bone plate 180 (not illustrated) can have similar features as those described with respect to the bone facing surface 50 of the bone plate 20. For example, the bone facing surface can have regions configured for bending the same as or similar to those described for the bone plate 20.

In FIGS. 6A and 6B, the bone plate 180 has a length defining two central longitudinal axes L1 and L2 which are shown as parallel axes. In addition to regions 55A, 55B, 55C, and 55D having fixation holes 60A, 60B, 60C, and 60D respectively, the bone plate 180 also includes regions 55E, 55F, 55G, and 55H having fixation holes 60E, 60F, 60G, and 60H respectively. Additional branches 130 are used to connect the regions 55A and 55E; 55B and 55F; 55C and 55G; and 55D and 55H. The bridge 100 connects the portion of the bone plate 180 extending along the axis L1 to the portion of the bone plate 180 extending along the axis L2. Depending on the application of the bone plate 180, the bridge 100 can extend between the axes L1 and L2 at any location. The bone plate 180, similar to the bone plate 170, defines the width W4 at the regions 55A, 55B, 55C, 55D, 55E, 55F, 55G, and 55H, a width W5 along the bridge 100, and a width W6 along the branches 130.

FIGS. 7A and 7B show a side elevational view and a perspective view, respectively, of the bone plate 20 discussed above with respect to FIGS. 1-3B. While the foregoing discussion of FIGS. 7A and 7B is described with respect to the bone plate 20, it should be appreciated that other bone plate configurations as described herein can be implemented according to FIGS. 7A and 7B.

In FIG. 7A, the bone plate 20 is positioned such that the bone facing surface 50 is facing at least one bone 190. As the bone plate 20 is moved closer to the bone 190, the pads 70 and 110 can come into contact with the bone 190. Contacting the bone 190 with the pads 70 and 110, as opposed to contacting the bone 190 across the entire bone facing surface 50, can help to decrease trauma to the periosteal membrane of the bone 190, allowing for increased blood flow to promote healing. The bone plate 20 may also be positioned such that the bridge 100 extends across a target area 195. In the illustration of FIG. 7A, the target area 195 is depicted as a fracture of the bone 190. However, in other applications, target area 195 may be a joint separating two different bones, such as a metatarsal-cuneiform joint, or across other areas needing bone fixation at adjacent locations.

The bone plate 20 as shown in FIGS. 7A and 7B has attachment members 200 positioned at least partially within the fixation holes 60A, 60B, 60C, and 60D. The attachment members 200 may be removably inserted into fixation holes 60A-D and project away from the top surface 40. For example, where the fixation holes 60A, 60B, 60C, and 60D are threaded, the attachment members 200 can also be threaded so as to be attached within the fixation holes 60A, 60B, 60C, and 60D. The attachment members 200 may function as drill or tool guides, forming a co-axial channel with a corresponding fixation hole through which a drill or tool can be inserted. Although the attachment members 200 are illustrated as cylinders projecting away from the top surface 40, the attachment members can have other shapes and configurations. As one example, the attachment members 200 may have a polygonal cross-sectional shape (e.g., square, hexagon, octagon), providing angular external surfaces on which to clamp tools during assembly, removal, and/or use.

The attachment members 200 can be utilized, for example, to assist in locating and aligning pilot tools and drill bits and/or bending the bone plate 20 to better align with a contour of the bone 190 or other anatomy. For instance, it may be necessary to bend the bone plate 20 so that each of the pads 70 and 110 is in contact with the bone 190. The attachment members 200 can be, for example, cylindrical along an axial length of the attachment members 200 and include apertures that are aligned with the respective fixation holes 60A, 60B, 60C, and 60D. As shown, the attachment members 200 have an elongated aperture, relative to the fixation holes 60A, 60B, 60C, and 60D, that can help align tools and/or drill bits used during various applications of the bone plate 20. Also, the extension of the attachment members 200 out from the top surface 40 can allow for greater leverage for bending the bone plate 20. The attachment members 200 are illustrated as having a length greater than a maximum thickness of bone plate 20, although other sized attachment members can be used depending on the application.

FIG. 8 illustrates a perspective view of a further embodiment of a bone plate 210, where like reference numerals refer to like components discussed above. The bone plate 210 is similar to the bone plate 20, except that the bone plate 210 has the branch 130 connecting the region 55A extending perpendicular to the axis L while the branch 130 connecting the regions 55C and 55D extends along the axis L. The attachment members 200 are again shown configured partially within the fixation hole 60A, 60B, 60C, and 60D at the regions 55A, 55B, 55C, and 55D.

Fasteners 220, such as bone screws having a head and a threaded shaft, are also shown in FIG. 8. The fasteners 220 can be inserted through the fixation holes 60A, 60B, 60C, and 60D such that an end of the fasteners 220 extends into a bone to secure the bone plate 210 to the bone. Further, a proximal region of the fasteners may engage with threaded portions of the fixation holes. The fasteners may include any suitable diameter and length. In some embodiments, the fasteners include a thread diameter of about 2 to about 3.5 mm, and a length of about 10 to about 35 mm. Depending on the geometry of the attachment members 200, if used, the fasteners 220 may be inserted through the fixation holes 60A, 60B, 60C, and 60D after the attachment members 200 have been removed from the fixation holes 60A, 60B, 60C, and 60D. In some embodiments, not shown, a washer is provided for positioning between a fastener and a bone, where the fastener does not extend through a bone plate. Such an embodiment is useful for connecting adjacent bones with a fastener and/or inserting a fastener across a joint space.

Figure 9:
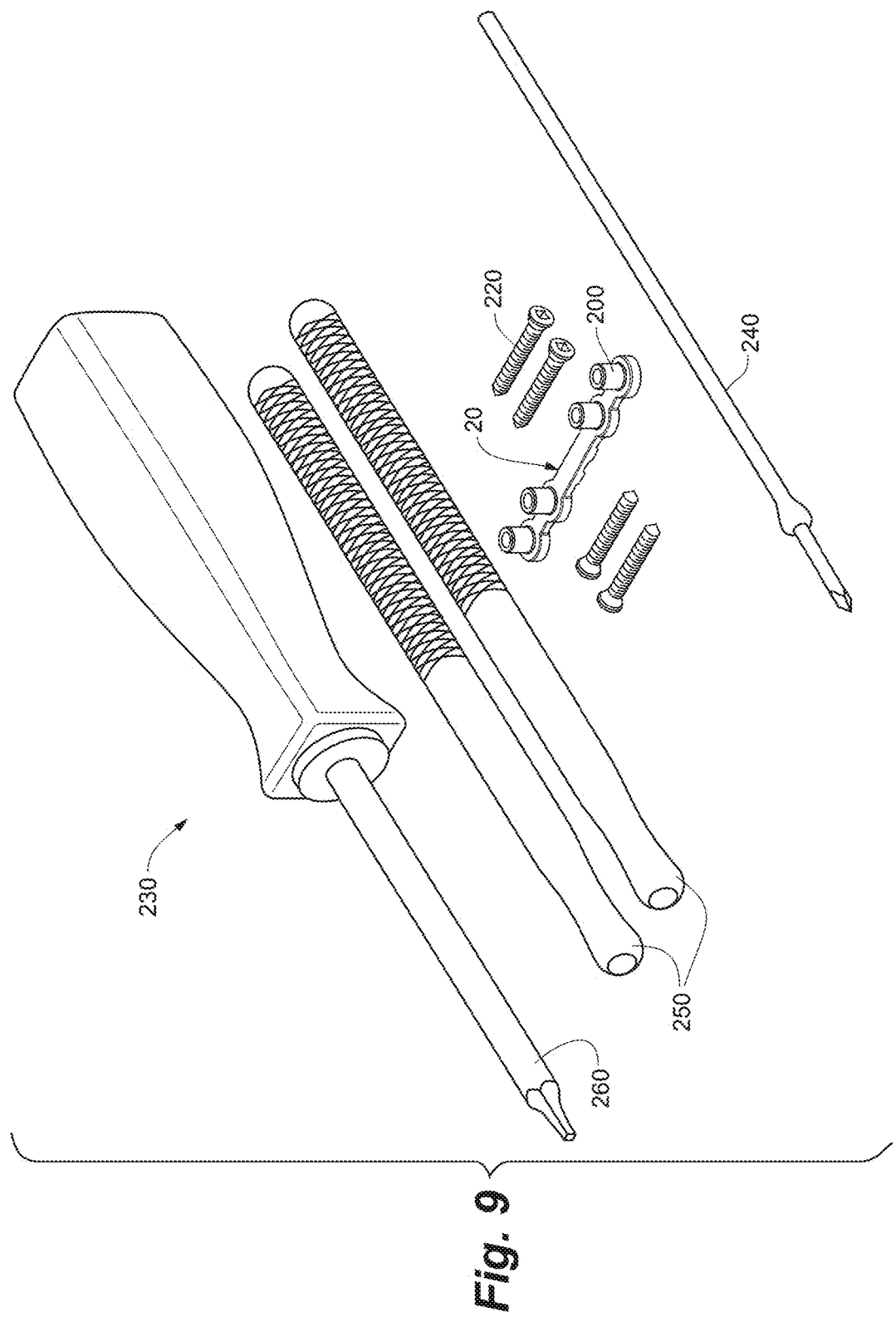
FIG. 9 is a perspective view of a kit for use with any of the described embodiments of the bone plate.

A bone plate according to the disclosure may be provided as part of a kit that is intended to be used by a clinician during a procedure. Such a kit can include one or more embodiments of a bone plate according to the disclosure, as well as attachment members, fixation screws, one or more pilot tools, one or more bending tools, and/or one or more drive members. FIG. 9 shows a perspective view of an exemplary kit 230. The kit 230 includes a bone plate 20, the attachment members 200, and fasteners 220. At least one washer (e.g., one washer for each fixation hole provided on the bone plate included in the kit), not shown, may be provided for positioning between a fastener and a bone. In addition, kit 230 includes a pilot tool 240, bending tools 250, and drive member 260.

The pilot tool 240 may be used to create an initial hole in a bone. Creating this initial hole with the pilot tool 240 can assist in later inserting the fastener 220 into the bone. The bending tools 250 can each have an end with a geometry adapted to mate with an end of the attachment members 200. Once one bending tool 250 has been mated to an attachment member 200, it may be desirable to mate a second bending tool 250 to a second attachment member 200 depending on the desired curvature of the bone plate 20. The bending tools 250 can then be used to bend the bone plate 20 to better align with the contour of the bone to which the bone plate 20 is to be fixed as desired. For example, it can be beneficial to bend the bone plate 20 such that any pads on the bone plate 20 are in contact with the bone. The drive member 260 can have an end adapted to mate with the attachment members 200 so that the drive member 260 may be used to both insert and remove the attachment members 200 from the fixation holes of the bone plate 20. The drive member 260 can also be used to insert the fasteners 220 through the fixation holes in the bone plate 20 and into the bone to which the bone plate 20 is to be fixed. The kit 230 including the described components may be included in a sterile pack for a single use.

In an exemplary embodiment, the kit 230 contains two bone plates (e.g., at least one of which includes a helical curvature) and a first set of fasteners with a first length, a second set of fasteners with a second length, a third set of fasteners with a third length, and a fourth set of fasteners with a fourth length, where each of the first, second, third, and fourth lengths are different. In another exemplary embodiment, the kit 230 includes two bone plates (e.g., at least one of which includes a helical curvature) and a first set of fasteners with a first length, a second set of fasteners with a second length, and a third set of fasteners with a third length, where each of the first, second, and third lengths are different. In yet another exemplary embodiment, the kit 230 contains two bone plates (e.g., at least one of which includes a helical curvature) and a first set of fasteners with a first length and a second set of fasteners with a second length, where the first and second lengths are different. In yet another exemplary embodiment, the kit 230 contains two bone plates (e.g., at least one of which includes a helical curvature) and only one set of fasteners each having the same length.

A bone plate and/or bone plate kit according to the disclosure can be used in a procedure to fixate one or more bones (e.g., two bones). For example, a site at which the bone plate is to be applied can be prepared for application of the bone plate. Attachment members can be secured in one or more of the fixation holes of the bone plate. If needed, the bone plate may be bent to align with a contour of the bone or other anatomy to which the bone plate is to be fixated. The bone plate can be aligned along this bone or anatomy, for instance, such that any pad on the bone plate's bone facing surface is made to contact the bone or anatomy. Pilot holes aligned with the fixation holes can be created in the bone. Any attachment members provided may be removed from the bone plate. The bone plate can then be attached to the bone or anatomy using appropriate fasteners, such as bone screws. After attaching the bone plate to the bone or anatomy, the surgical site can be closed.

In some applications, it may be desirable to attach more than one bone plate to a particular bone or anatomy. In these applications, two or more bone plates may be aligned with respect to the bone or bones being fixated such that the two or more bone plates reside in different planes. For example, two bone plates can be attached to bone(s) with the two bone plates positioned approximately 90 degrees, with respect to each other, along the outer circumference of the bone(s) (e.g., left side and top, or top and right side). In certain embodiments, the longitudinal axes of the bone plates can be substantially parallel. This can be beneficial to provide strong fixation across multiple planes.

As discussed above with respect to FIGS. 1-3, the bone plate 20 may have a generally helical curvature 62 that positions a proximal region 51 containing one or more fixation holes in a different plane than a distal region 52 also containing one or more fixation holes. The helical curvature 62 may be formed by bending and/or twisting the body 30 of the bone plate 20. For example, the helical curvature 62 may be formed by imparting at least one bend to the elongated body that angles the proximal region 51 toward the distal region 52 and at least one twist to the elongated body that rotates the proximal region 51 relative to the distal region 52 around the elongated body. The at least one bend may be continuous with the at least one twist along the length of the body 30 such that, proceeding along the length of the body, the bend transitions into the twist without an intervening portion of body 30 that is neither bent nor twisted. In other configurations, the at least one bend is discontinuous with the at least one twist along the length of the body 30 such that, proceeding along the length of the body, the bend transitions into the twist with an intervening portion of body 30 that is neither bent nor twisted.

In applications where the bone plate 20 is configured with at least one bend and at least one twist, the bone plate may have only a single bend and/or single twist or may have multiple bends and/or multiple twists. For example, the bone plate 20 may have a bend that angles the proximal region 51 toward the distal region 52, a twist that rotates the proximal region 51 relative to the distal region 52, and another bend that angles the proximal region 51 further toward or away from the distal region 52. The angle of the first bend may be similar or different (e.g., greater or smaller) than the angle of the second bend. As another example, the bone plate 20 may have a twist that rotates the proximal region 51 relative to the distal region 52, a bend that angles the proximal region 51 toward the distal region 52, and another twist that further rotates the proximal region 51 relative to the distal region 52. Other configurations of bends and twists are possible.

Figure 10A:
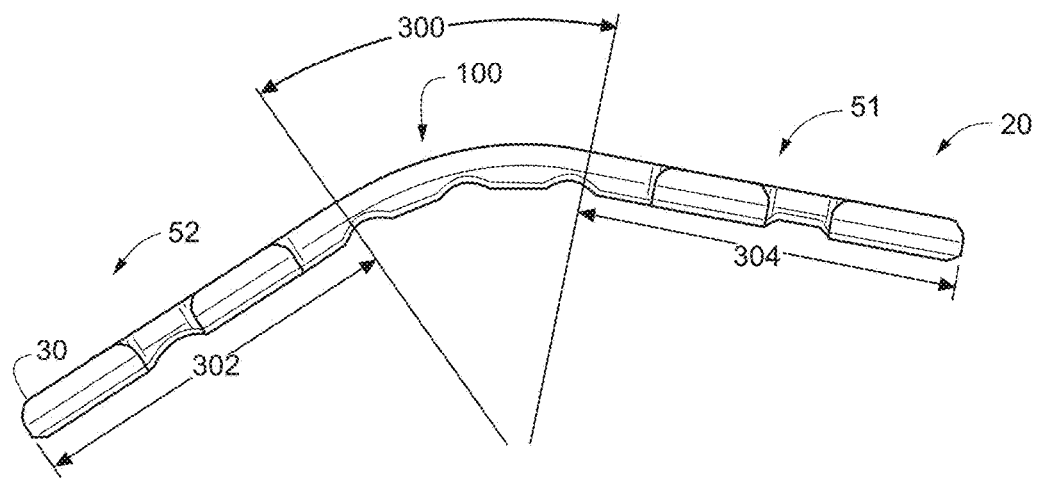
FIGS. 10A-10C illustrate example process steps for forming a bone plate with an example helical curvature.
Figure 10B:
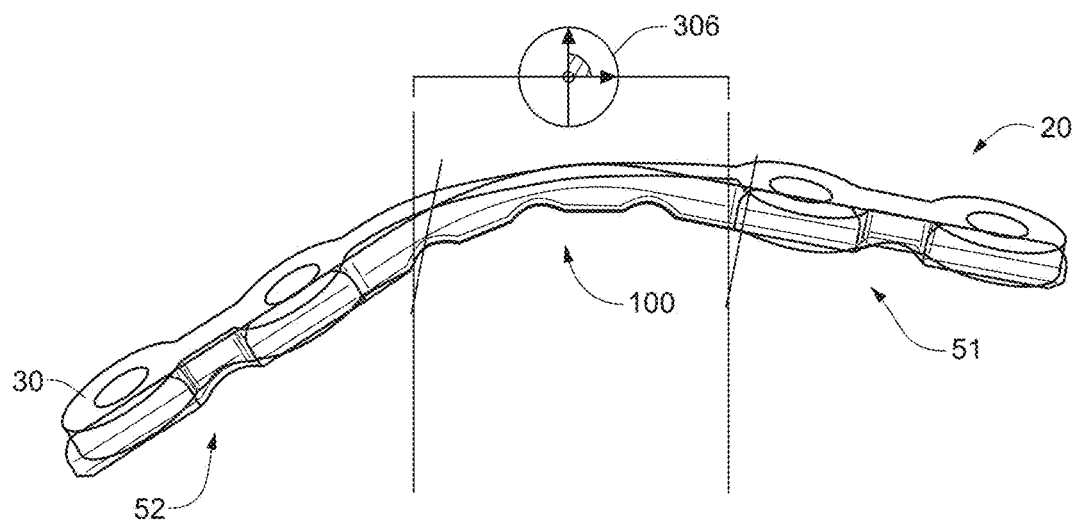
Figure 10C:
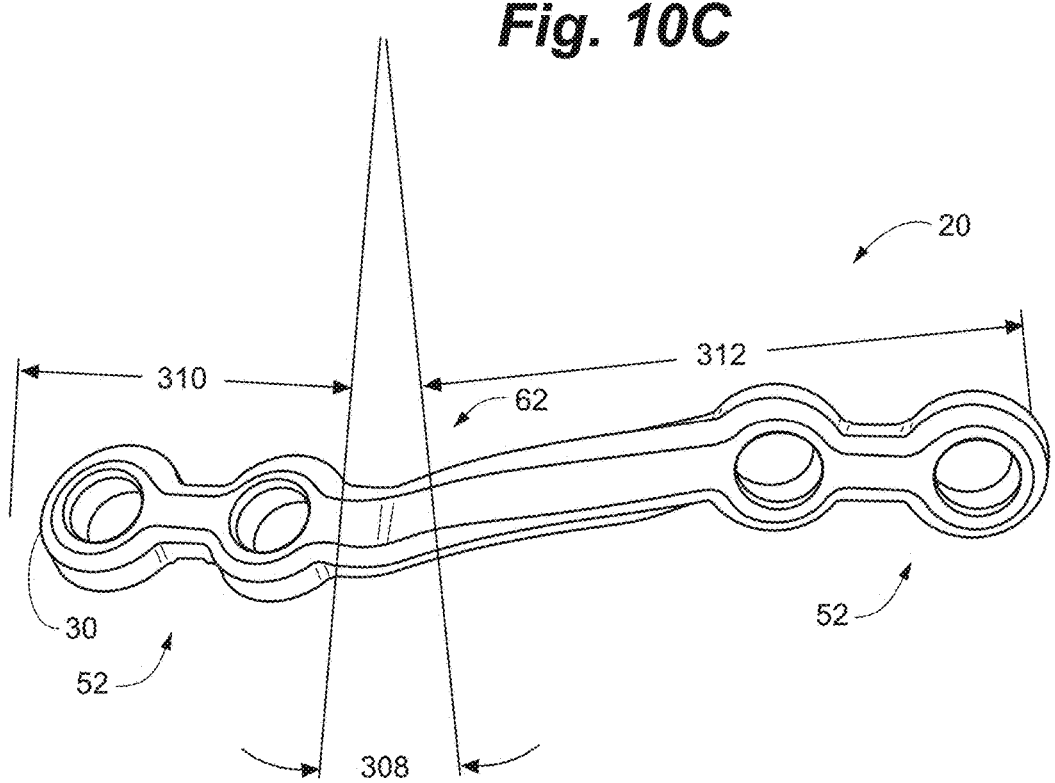

FIGS. 10A-10C illustrate example process steps for forming an example helical curvature 62 in the bone plate 20. Starting with a flat or planar bone plate 20, the bone plate is bent in FIG. 10A to impart a bend 300 between the proximal region 51 and the distal region 52. The bend 300 in the illustrated example is centered between a first section 302 of the body 30 containing the distal region 52 and a second section 304 of the elongated body containing proximal region 51. The bend 300 as illustrated angles the proximal region 51 toward the distal region 52, positioning the two regions closer together as compared to when the bone plate 20 is planar. In some examples, the bend ranges from 45° to 135°, such as from approximately 75° to approximately 105°.

In the illustrated example, the bone plate 20 containing bend 300 is twisted as shown in FIG. 10B to impart a twist 306 between the proximal region 51 and the distal region 52. The twist 306 is illustrated schematically as a degree of angular rotation of the proximal region 51 relative to the distal region 52 about an axis extending through the body 30. In particular, in FIG. 10B, the twist 306 is imparted over a section of body 30 containing bend 300. For example, the body 30 may be twisted along the section of body 30 containing the bend 300, or portion thereof, e.g., such that the twist 306 extends concurrent with at least a portion of the bend 300 along the length of the elongated body. In other examples, the twist 306 may be imparted to a section of the body 30 separate from the section containing bend 300. In some examples, the degree of angular rotation forming the twist 306 ranges approximately 15° to approximately 60°. In other examples, the degree of angular rotation forming twist 306 ranges approximately 75° to approximately 105°. Other degrees of angular rotation are also possible.

In FIG. 10C, the bone plate 20 containing bend 300 and twist 306 is further bent to impart a second bend 308. The second bend 308 is centered distally of the section of the body 30 containing the bend 300 and the twist 306, although in other examples, the second bend may be centered proximally of the section containing the bend 300 and the twist 306, or the second bend 308 be formed in a section of the elongated body also containing the bend 300 and the twist 306. As illustrated, the second bend 308 angles the distal region 52 farther away from the proximal region 51 than before imparting the bend (e.g. such that a distal end of the elongated body is farther away from a proximal end of the body). In some examples, the second bend ranges from 2° to 75°, such from approximately 5° to approximately 45°.

In FIGS. 10A-10C, helical curvature 62 is formed by a combination of the bend 300, the twist 306, and the second bend 308, collectively shaping the body 30 into a generally helical shape. While FIGS. 10A-10C illustrate one exemplary process for forming helical curvature 62, variations of the process are possible. For example, although FIGS. 10A-10C illustrate a sequential formation of bend 300 followed by twist 306 and the second bend 308, the order in which each of these features are formed in the elongated body may be rearranged. As another example, the bone plate 20 may include fewer bends or more bends than illustrated and/or may include more than one twist.

In addition, while FIGS. 10A-10C illustrate a process for forming bone plate 20 by bending and twisting a body that is initially planar, the bone plate may be formed using other fabrication techniques. For example, the bone plate 20 may be machined, forged, cast, molded, or otherwise fabricated to have the defined shape, size, and/or structural features. As one example, the bone plate 20 may be machined out of a single piece of material. This may improve the inherent mechanical properties of the bone plate 20 as compared to when the bone plate is formed using other techniques.

Although the present invention has been described with reference to certain disclosed embodiments, the disclosed embodiments are presented for purposes of illustration, and not limitation, and other embodiments of the invention are possible. Those of ordinary skill in the art will appreciate that various changes, adaptations, and modifications may be made without departing from the spirit of the invention.

The invention claimed is:

1. A bone plate comprising:
   a body having a length defining a central longitudinal axis extending from a proximal region of the body to a distal region of the body and a width defining an extent of the bone plate transverse to the central longitudinal axis, wherein the body includes a top surface and a bone facing surface opposite the top surface;
   a helical curvature between the proximal and distal regions of the body comprising both a bend of the body along the central longitudinal axis and a twist of the body about the central longitudinal axis, wherein the distal region lies in a first plane corresponding to a plantar region of a first bone to which the bone plate is configured to be attached and the proximal region lies in a second plane offset from the first plane both along and about the longitudinal axis such that the helical curvature provides a transition from the first plane to the second plane, the second plane corresponding to a medial region of a second bone to which the bone plate is configured to be attached; and
   a first fixation hole in the proximal region and a second fixation hole in the distal region, wherein the first fixation hole and second fixation hole each extend through the body from the top surface to the bone facing surface.

2. The bone plate of claim 1, wherein the twist of the body about the central longitudinal axis ranges from 25° to 100°.

3. The bone plate of claim 2, wherein the bend of the body along the central longitudinal axis ranges from 45° to 135°.

4. The bone plate of claim 1, further comprising:
   a pad extending out a distance from a first surface at a location on the bone facing surface adjacent the first fixation hole.

5. The bone plate of claim 1, wherein the body comprises a malleable material.

6. The bone plate of claim 1, wherein the helical curvature is pre-formed.

7. The bone plate of claim 1, wherein the bone plate is included in a kit.

8. The bone plate of claim 1, further including a third fixation hole in the proximal region and a fourth fixation hole in the distal region, wherein the third fixation hole and fourth fixation hole each extend through the body from the top surface to the bone facing surface.

9. The bone plate of claim 1, wherein the medial region comprises a medial-dorsal region of the second bone.

10. The bone plate of claim 1, wherein the first bone is a metatarsal and the second bone is a cuneiform.

11. The bone plate of claim 10, wherein the metatarsal is a first metatarsal and cuneiform is a medial cuneiform.

* * * * *